United States Patent
Ko et al.

(10) Patent No.: US 6,815,459 B2
(45) Date of Patent: Nov. 9, 2004

(54) SELENO COMPOUNDS CONTAINING NITRONE MOIETY, THEIR PREPARATION AND THEIR THERAPEUTIC USES

(75) Inventors: Sung-Bo Ko, Taejon (KR); Eu-Gene Oh, Taejon (KR); Eon-Kyeom Kim, Taejon (KR); Won-Yeob Kim, Taejon (KR); Dennis W. Choi, St. Louis, MO (US); Laura L. Dugan, St. Louis, MO (US); Jae-Young Koh, Seoul (KR); Moo-Ho Won, Chuncheon (KR); Myung-Bok Wie, Chuncheon (KR)

(73) Assignee: Sam-Sung Electronics Co., Ltd., Suwon (KR)

( * ) Notice: Subject to any disclaimer, the term of this patent is extended or adjusted under 35 U.S.C. 154(b) by 0 days.

(21) Appl. No.: 10/456,268

(22) Filed: Jun. 6, 2003

(65) Prior Publication Data

US 2003/0220337 A1 Nov. 27, 2003

Related U.S. Application Data

(63) Continuation of application No. PCT/KR01/01275, filed on Jul. 26, 2001.

(51) Int. Cl.$^7$ ........................ A61K 31/41; C07D 293/12
(52) U.S. Cl. ............... 514/359; 514/245; 514/252.05; 514/255.05; 514/256; 514/275; 514/338; 544/212; 544/238; 544/328; 544/331; 544/405; 546/268.4; 548/120; 548/121
(58) Field of Search ........................ 514/359, 245, 514/254, 338, 256, 252.05, 255.05, 275; 548/121, 120; 546/270; 544/238, 212, 322, 405, 328, 331

(56) References Cited

U.S. PATENT DOCUMENTS

5,008,394 A 4/1991 Günther et al. ............. 544/121
5,827,880 A 10/1998 Malroy-Camine et al. .. 514/492

FOREIGN PATENT DOCUMENTS

JP WO98/08831 3/1998

OTHER PUBLICATIONS

Parnetti, L. et al., Cognitive Enhancement Therapy for Alzheimer's Disease Drugs, 53:752–768 (1997).
Grisar J. M. et al., 2,3–Dihydro–1–benzofuran–5–ols as Analogues of α–Tocopherol That Inhibit in Vitro an ex Vivo Lipid Autoxidation and Protect Mice against Central Nervous System Trauma, J. Med. Chem., 38:453–458(1995).
Thomas G. Back and Brian P. Dyck, A Novel Camphor–Derived Selenenamide That Acts as a Glutathione Peroxidase Mimetic, J. Am. Chem. Soc., 119:2079–2083 (1997).
Sies, et al., Ebselen as a Glutathione Peroxidase Mimic and as a Scavenger of Peroxynitrite, Adv. Pharmaco., 38:229–246 (1997).
Koh, et al., The Role of Zinc in Selective Neuronal Death after Transient Global Gerebral Ischemia, Science, vol. 272, 1013–1016 (1996).
Kim, et al., Zinc–Induced Cortical Neuronal Death with Features of Apoptosis and Necrosis: Mediation by Free Radicals, Neuroscience, 89:175–182 (1999).

*Primary Examiner*—Richard L. Raymond
(74) *Attorney, Agent, or Firm*—Knobbe Martens Olson & Bear LLP.

(57) ABSTRACT

The present invention provides novel seleno compounds containing nitrone moiety, a process for preparing the same, the use of the novel compounds as therapeutics for treating and/or preventing various medical dysfunctions and diseases arising from reactive oxygen species, in particular stroke, Parkinson's disease, Alzheimer's disease. The compounds of the invention have similar or superior lipid peroxidation (LPO) inhibition activity to the reference compounds. While showing lower toxicity and better water solubility, they also effectively inhibit the cerebral neuronal cell death caused by ROS and show neuroprotective effects against ischemic neuronal degeneration.

15 Claims, 7 Drawing Sheets

Sham   Global ischemic control   Example 5

SELENO COMPOUNDS CONTAINING NITRONE MOIETY, THEIR PREPARATION AND THEIR THERAPEUTIC USES

RELATED APPLICATIONS

This application is a continuation under 35 U.S.C. §365 (c) claiming the benefit of the filing date of PCT Application No. PCT/KR01/01275 designating the United States, filed Jul. 26, 2001. The PCT Application was published in English as WO 03/010154 A1 on Feb. 6, 2003. The contents of the international application No. PCT/KR01/01275 and the publication WO 03/010154 A1 are incorporated herein by reference in their entirety.

BACKGROUND OF THE INVENTION

1. Field of the Invention

The present invention relates to novel seleno compounds containing nitrone moiety, their preparation and pharmaceutical compositions containing the novel compounds as active ingredients, more particularly, to novel seleno compounds containing nitrone moiety, a process for the preparation of the same, the use of the novel compounds as therapeutics for treating and/or preventing various medical dysfunctions and diseases caused by reactive oxygen species (ROS), in particular stroke, Parkinson's disease, and Alzheimer's disease.

2. Description of the Prior Art

According to Harman's free-radical theory of ageing, successive oxidation attacks create "oxidative stress" conditions, that is, create an imbalance between the protective systems in favour of the pro-oxidants.. Such attacks result in numerous molecular modifications, especially of polyunsaturated membrane lipids, proteins and nucleic acids. Human and animal organisms possess various defense mechanisms that act in synergy. Those mechanisms are of an enzymatic nature (superoxide dismutase, catalase, and glutathione peroxidase) or of a non-enzymatic nature (such as vitamins E and C, which enable physiological control of free-radical activity). With ageing, however, that protection becomes less efficient, not to say inefficient, especially as a result of the decreased activity of a large number of enzymes including those involved in such defense mechanisms. Consequently, for some disorders associated with ageing, such as atherosclerosis, cataract, non-insulin-dependent diabetes, cancer or chronic neurodegenerative disorders, numerous studies have been able to demonstrate that such conditions are associated with those "oxidative stress" conditions.

The central nervous system is especially sensitive to "oxidative stress" because of its high oxygen consumption, the relatively low levels of its antioxidant defenses and the high iron concentration of some cerebral regions. This explains why "oxidative stress" might be one of the main etiological factors of cerebral ageing, as well as of acute central nervous system disorder such as stroke, neurodegenerative disorders such as Parkinson's disease, Alzheimer's disease, and neurodegeneracies of the basal ganglia. The rate of occurrence of neurodegenerative disorders of central nervous system increases worldwide. Stroke occupies the third highest cause of death following cardiovascular diseases and malignant tumors (see: Parnetti, L. et al., Drug, and 53:752 (1997)).

Antioxidants protecting neuron cell of brain from oxidative stress include vitamin E derivatives such as Trolox (see: J. Med. Chem., 38:453 (1995)), glutathione peroxidase (hereinafter, referred to as "GPx") mimics (see: Daiichi Pharmaceutical Co., Ltd., Annual Report (1999); WO 9808831; U.S. Pat. No. 5,008,394; J. Am. Chem. Soc., 119:2079–2083 (1997); Adv. Pharmacol., 38:229 (1996)), superoxide dismutase (SOD) mimics (see: U.S. Pat. No. 5,827,880), and spin trapping agents (see: J. Med. Chem., 39:4988 (1996); U.S. Pat. No. 5,475,032).

A GPx mimic is a synthesized compound mimicking the function of the selenocystein from GPx active site. A well-known GPx mimic, Ebselen seems to have no major toxicity in preclinical and clinical tests and it is proposed as a potential drug for stroke. Ebselen is, however, very little soluble in water, even in the presence of an excess of glutathione (GSH), which limits its pharmacological applications.

Spin trapping agents may be developed as an antioxidant if they can trap hazardous free radicals enough, which include α-phenyl-N-tert-butylnitrone (PBN), and various derivatives of PBN have been developed. Generally, nitrone moiety increases the solubility of compounds in water. However, it has revealed shortcomings such as a low lipid peroxidation inhibition activity in vitro and a low protection of brain cells in vivo (see: Fevig, Thomas L. et al., J. Med. Chem., 39:4988–4996 (1996)).

SUMMARY OF THE INVENTION

The present inventors synthesized novel compounds by introducing spin trapping agent, i.e., nitrone moiety into GPx mimic, Ebselen, which have not only increased solubility in water and low toxicity but also peroxidase function and radical trapping function. Also, they found that the said compounds have effective antioxidant activity for the treatment and prevention of cell death of brain cells while showing low toxicity. As a result, the said compounds could be potential drug candidates for the treatment and prevention of cell death of brain cells.

The first object of the present invention is, therefore, to provide new type of antioxidants which are GPx mimics containing spin trapping moiety.

The second object of the invention is to provide a process for preparing the said antioxidants.

The third object of the invention is to provide pharmaceutical compositions comprising the said antioxidants as an active ingredient for the treatment and prevention of medical dysfunctions and diseases such as stroke, Parkinson's disease, and Alzheimer's disease caused by reactive oxygen species.

The fourth object of the invention is to provide a method for treating a living body afflicted with a condition requiring an antioxidant agent, in particular acute and progressive neurodegenerative disorders, by way of administering to the living body the said pharmaceutical preparations.

BRIEF DESCRIPTION OF THE DRAWINGS

The above and the other objects and features of the present invention will become apparent from the following descriptions given in conjunction with the accompanying drawings, in which:

FIG. 11-b is a photomicrograph showing the protection level of cell damage in case of the treatment of the compound of the invention after ischemia.

DETAILED DESCRIPTION OF THE INVENTION

Figure 1:
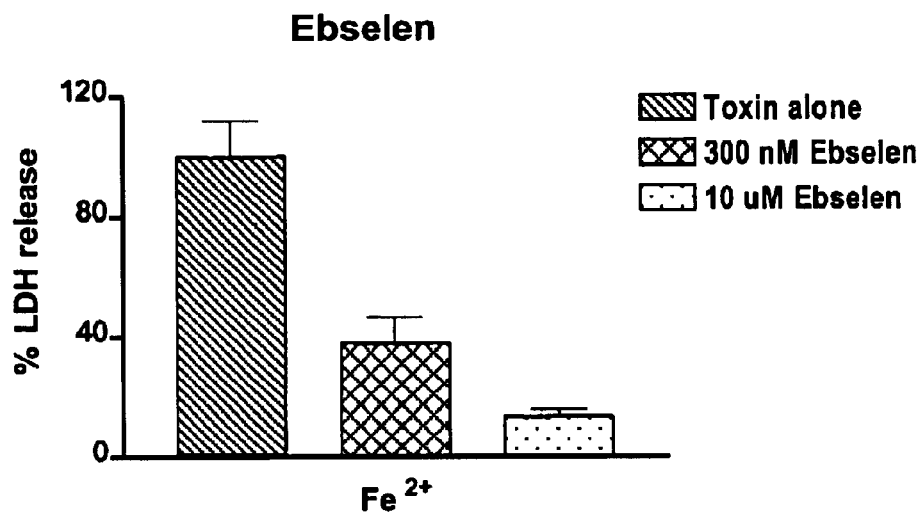
FIG. 1 is a graph showing the results of combined treatment of Ebselen and $Fe^{2+}$ toxin.

In the first aspect, the present invention provides novel antioxidants with the following general formula (I), which have both peroxidase activity and free radical trapping activity as a dual function:

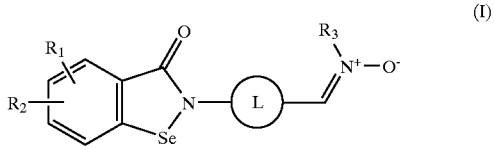

(I)

wherein, $R_1$, and $R_2$ which may be the same or different from each other, represent hydrogen, halogen, $C_{1-4}$-alkyl, $C_{1-4}$-alkoxy, hydroxy, trifluoromethyl, nitro, or $R_1$ and $R_2$ together denote methylenedioxy;

L denotes phenyl, $C_{1-4}$-alkylphenyl, heterocyclic unsaturated or saturated radical having 1 to 4 heteroatoms of elements nitrogen, oxygen, and/or sulfur from the group comprising furanyl, oxazolyl, isooxazolyl, thiophenyl, thiazolyl, isothiazolyl, pyrrolyl, imidazolyl, pyrazolyl, thiadiazolyl, pyridyl, pyrimidinyl, pyrazinyl, pyridazinyl, benzothiazolyl, benzoimidazolyl, benzotriazolyl, triazinyl, triazolyl, it being possible for the heterocyclic radical to be substituted once or twice, identically or differently, by halogen, $C_{1-2}$-alkyl, $C_{1-4}$-alkoxy, $C_{1-4}$-alkylthio, hydroxy, mercapto, trifluoromethyl, nitro, phenyl, nitrile, carboxy or $C_{1-4}$-alkoxycarbonyl; and, $R_3$ represents alkyl, substituted alkyl, alkenyl, alkynyl, aralkyl, aryl, cycloalkyl or cycloalkenyl.

In this context, preferred compounds include derivatives in which $R_1$ and $R_2$ can be identical or different and, independently of one another, denote hydrogen, fluorine, chlorine, bromine, hydroxy, methyl, ethyl, methoxy, trifluoromethyl, nitro or methylenedioxy;

$R_3$ denotes alkyl, substituted alkyl, aralkyl, aryl, and cycloalkyl; and,

L denotes phenyl, methylphenyl, ethylphenyl, heterocyclic unsaturated or saturated radical having 1 to 4 heteroatoms of the elements nitrogen, oxygen, and/or sulfur from the group comprising the furanyl, oxazolyl, thiophenyl, thiazolyl, pyrrolyl, imidazolyl, pyrazolyl, pyridyl, pyrimidinyl, pyrazinyl, pyridazinyl, benzothiazolyl, triazinyl, triazolyl, it being possible for the heterocyclic radical to be substituted once or twice, identically or differently, by fluorine, chlorine, bromine, methyl, ethyl, butyl, methoxy, ethoxy, methylmercapto, ethylmercapto, hydroxy, mercapto, trifluoromethyl, nitro, phenyl, nitrile, carboxy or methoxycarbonyl and ethoxycarbonyl.

More preferred compounds include derivatives in which $R_1$ and $R_2$ can be identical or different and, independently of one another, denote hydrogen, fluorine, chlorine, methyl, methoxy, trifluoromethyl, nitro or methylenedioxy;

L denotes phenyl, methylphenyl, ethylphenyl, heterocyclic unsaturated or saturated radical having 1 to 4 heteroatoms of the elements nitrogen, oxygen, and/or sulfur from the group comprising the furanyl, oxazolyl, thiophenyl, thiazolyl, pyrrolyl, imidazolyl, pyridyl, pyrimidinyl, benzothiazolyl, it being possible for the heterocyclic radical to be substituted once or twice, identically or differently, by fluorine, chlorine, bromine, methyl, methoxy, ethoxy, methylmercapto, hydroxy, mercapto, nitro, phenyl, nitrile, carboxy or methoxycarbonyl and ethoxycarbonyl; and, $R_3$ denotes alkyl, cycloalkyl.

The compounds of the invention possess similar or superior lipid peroxidation (LPO) inhibition activity to the reference compounds of S-PBN and Ebselen. While showing lower toxicity and better water solubility, they also effectively inhibit the cerebral neuronal cell death caused by ROS and show neuroprotective effects against ischemic neuronal degeneration.

The compounds of the invention, particularly the compound synthesized in Example 5 below, have a very low toxicity $LD_{50} \geqq 7,000$ mg/kg in the case of oral administration in rats, and $\geqq 800$ mg/kg in the case of intraperitoneal administration in rats. Therefore, one of the advantages of the present invention is that the novel compounds can be administered at vastly higher levels than certain other known antioxidants, such as Ebselen ($LD_{50}$ values of Ebselen obtained in mice were $\geqq 6,810$ mg/kg in the case of oral administration, and 740 mg/kg in the case of intraperitoneal administration. Similarly, the $LD_{50}$ values of Ebselen obtained in rats were $\geqq 6,810$ mg/kg in the case of oral administration, and 580 mg/kg in the case of intraperitoneal administration). Accordingly, large doses of the novel compounds may be administered immediately post stroke or other traumas to reduce oxidative damage significantly.

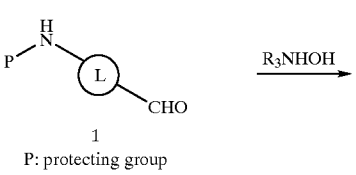

1

P: protecting group

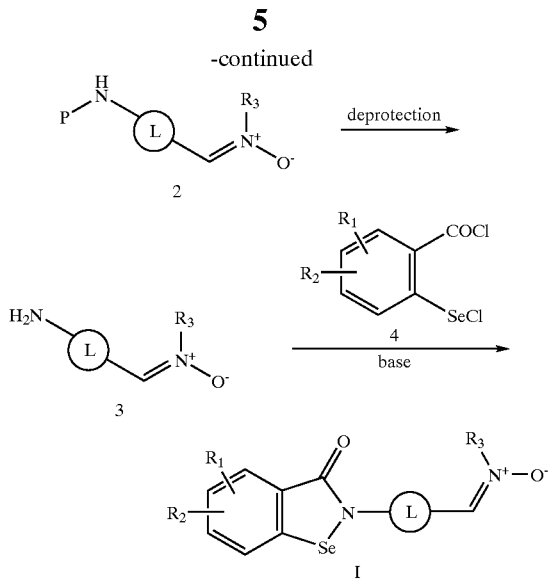

In the second aspect, the present invention provides a process for the preparation of the compounds of formula (I) above, which is illustrated in the following reaction scheme:

N-protected aldehydes having proper linkers (L), represented as "1", react with alkylhydroxylamines ($R_3$NHOH) to give nitrones shown as "2", which then undergo deprotection step to produce free amine nitrones represented as "3". Preferably, the alkylhydroxylamines are generated in situ from nitroalkanes, zinc, and acetic acid. Removal of the protection group is carried out preferably with trifluoroacetic acid in case the protection group is tert-butoxycarbonyl, or LiOH in case the protection group is acetyl.

Free amines of the compound shown as "3" react with o-chloroselenobenzoyl chlorides (represented as "4") in the presence of excess base, organic base, more preferably triethylamine, to generate seleno compounds containing nitrone moiety of formula (I).

In the third aspect, the present invention provides pharmaceutical compositions comprising a pharmaceutically acceptable carrier and a pharmaceutically effective amount of a compound of formula (I) above or pharmaceutically acceptable salts thereof.

In the fourth aspect, the present invention provides a method for treating a living body afflicted with a condition requiring an antioxidant, in particular acute and progressive neurodegenerative disorders, comprising a step of administering to the living body said pharmaceutical composition.

As previously mentioned, the compounds of the present invention have been proved to be effective anti-oxidants relieving various effects resulting from ROS. These compounds are useful as therapeutics for treating and/or preventing a wide variety of medical dysfunctions and diseases including, but not limited to, acute central nervous system (CNS) disorders and neurodegerative diseases.

The compounds of the invention as pharmaceuticals, are typically administered in the form of a pharmaceutical composition comprising at least one active compound of the invention and a pharmaceutically acceptable carrier or vehicle suitable for use in pharmaceutical compositions.

In general, the compounds of the invention are administered in a pharmaceutically effective amount. The amount of the compound actually administered will typically be determined by a physician, in light of relevant circumstances, including the condition to be treated, the chosen route of administration, the actual compound administered, the age, weight, and response of the individual patient, the severity of the patient's symptoms, and the like. The dosage used ranges from 10 mg to 500 mg in one or several administrations per day.

The pharmaceutical compositions of the invention can be administered by a variety of routes including oral, rectal, transdermal, subcutaneous, intravenous, intramuscular, and intranasal. Depending on the intended route of delivery, the compounds of this invention are preferably formulated as either injectable or oral compositions.

The compositions for oral administration can take the form of bulk liquid dilutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the seleno compounds containing nitrone moiety of the invention is usually a minor component (from about 0.1 to about 50% by weight or preferably from about 1 to about 40% by weight) with the remainder being various vehicles or carriers and processing acids helpful for forming the desired dosing form.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art. As before, the present compound in such compositions is typically a minor component, often being from about 0.05 to 10% by weight with the remainder being the injectable carrier and the like.

The components for orally administrable or injectable compositions are merely representative. Other materials as well as processing techniques and the like are set forth in Part 8 of Remington's Pharmaceutical Sciences, 17th edition, 1985, Mack Publishing Company, Easton, Pa., which is incorporated herein by reference.

The compounds of the invention can also be administered in sustained release forms or from sustained release drug delivery systems. A description of representative sustained release materials can be found in the incorporated materials in Remington's Pharmaceutical Sciences.

The following examples are provided to illustrate this invention and are not to be construed in any way as limiting the scope of this invention.

EXAMPLE 1

Synthesis of 2-[4-(N-isopropyl)nitronyl]phenyl-1,2-benzisoselenazol-3(2H)-one (8)

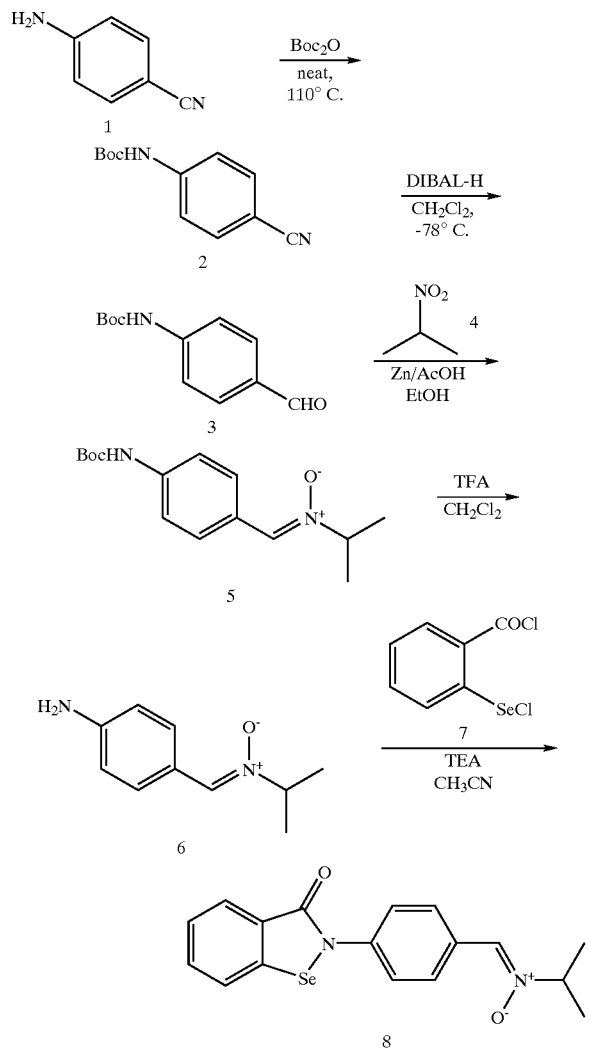

Step 1: Synthesis of 4-N-(1,1-dimethylethoxycarbonyl) aminobenzonitrile (2)

500 mg (4.23 mmol) of 4-aminobenzonitrile (1) and 1.90 g (8.70 mmol) of di-tert-butyl dicarbonate ($Boc_2O$) were added into a flask and the mixture was heated for 6 hours at 110° C. The reaction mixture was cooled to room temperature and purified by short flash column chromatography (silica, $CH_2Cl_2$:Hex:EtOAc=10:10:1) to give 630 mg (2.90 mmol) of compound 2 as a white solid in 68% yield.

$^1$H NMR ($CDCl_3$):7.58 (d, J=8.7 Hz, 2H), 7.48 (d, J=8.7 Hz, 2H), 6.65 (br s, 1H), 1.53 (s, 9H).

Step 2: Synthesis of 4-N-(1,1-dimethylethoxycarbonyl) aminobenzaldehyde (3)

To a solution of 600 mg (2.75 mmol) of nitrile 2 in $CH_2Cl_2$ (8 mL) were added 8.3 mL (8.3 mmol) of diisobutylaluminum hydride (DIBAL-H, 1.0 M soln in toluene) for 2 minutes at −78° C. After stirring for 1 hour at that temperature, 2 mL of MeOH was slowly added to the reaction mixture, and then the reaction mixture was warmed to room temperature. Diethyl ether and 0.5 N HCl solution were added and the organic layer was separated. The aqueous layer was re-extracted with diethyl ether. The combined organic layers were washed with saturated $NaHCO_3$ solution, dried over anhydrous $Na_2SO_4$, filtered, and concentrated under reduced pressure. The residue was purified by short flash column chromatography (silica, $CH_2Cl_2$:Hex:EtOAc=10:10:1 to 10:10:2) to give 585 mg (2.64 mmol) of compound 3 as a white solid in 96% yield.

$^1$H NMR ($CDCl_3$):9.89 (s, 1H), 7.83 (d, J=8.6 Hz, 2H), 7.53 (d, J=8.6 Hz, 2H), 6.70 (br s, 1H), 1.55 (s, 9H)

Step 3: Synthesis of N-isopropyl-α-[4-N-(1,1-dimethylethoxycarbonylamino)phenyl]nitrone (5)

422 mg (1.90 mmol) of compound 3, 680 mg (7.63 mmol) of 2-nitropropane (4), and 745 mg (11.40 mmol) of zinc were placed in a round-bottomed flask along with 95% ethanol (8 mL). The mixture was cooled to 0° C. and 0.87 mL (15.20 mmol) of acetic acid was added slowly with stirring. The solution was allowed to come to room temperature, stirred for 6 hours. $CH_2Cl_2$ was added to the reaction mixture and it was filtered through a Celite pad and concentrated under reduced pressure. The residue was purified by short flash column chromatography (silica, $CH_2Cl_2$:EtOAc=1:2) to give 500 mg (1.80 mmol) of compound 5 as a white solid in 95% yield.

$^1$H NMR ($CDCl_3$):8.21 (d, J=8.9 Hz, 2H), 7.42 (d, J=8.9 Hz, 2H), 7.37 (s, 1H), 6.61 (br s, 1H), 4.19 (septet, J=6.5 Hz, 1H), 1.52 (s, 9H), 1.50 (d, J=6.5 Hz, 6H).

Step 4: Synthesis of N-isopropyl-α-(4-aminophenyl)nitrone (6)

To a solution of 320 mg (1.15 mmol) of compound 5 in $CH_2Cl_2$ (10 mL) was added 1 mL of trifluoroacetic acid slowly at 0° C. The reaction mixture was warmed to room temperature and stirred for 16 hours. After concentration of the solution, the mixture was diluted with $CH_2Cl_2$ and saturated $NaHCO_3$ solution. The solution was saturated with NaCl and the organic layer was separated. The aqueous layer was extracted three times with $CH_2Cl_2$. The combined organic layers were dried over anhydrous $Na_2SO_4$ and concentrated under reduced pressure. The residue was purified by short flash column chromatography (silica, $CH_2Cl_2$:EtOAc:MeOH=5:5:1) to give 132 mg (0.74 mmol) of compound 6 as a yellow solid in 64% yield.

$^1$H NMR ($CDCl_3$): 8.12 (d, J=7.0 Hz, 2H), 7.27 (s, 1H), 6.68 (d, J=7.0 Hz, 2H), 4.19 (septet, J=6.5 Hz, 1H), 1.51 (d, J=6.5 Hz, 6H);

$^{13}$C NMR ($CDCl_3$): 149.08, 132.69, 131.04, 121.39, 114.66, 67.13, 21.23.

Step 5: Synthesis of 2-[4-(N-isopropyl)nitronyl]phenyl-1,2-benzisoselenazol-3(2H)-one (8)

To a solution of 75 mg (0.42 mmol) of compound 6 and 1.0 mL (7.17 mmol) of triethylamine in $CH_2Cl_2$ (3 mL) was slowly added 200 mg (0.79 mmol) of 2-chlorocarbonyl-benzeneselenenyl chloride (7) in $CH_2Cl_2$ (1.5 mL) at 0° C. After stirring for 4 hours at room temperature, the reaction mixture was concentrated under reduced pressure. The residue was purified by short flash column chromatography (silica, $CH_2Cl_2$:EtOAc=3:1 with 0 to 10% methanol) to give 83 mg (0.23 mmol) of compound 8 as a pale yellow solid in 55% yield.

$^1$H NMR ($CDCl_3$:$CD_3OD$=4:1):8.33 (d, J=8.8 Hz, 2H), 8.08 (dd, J=7.8 and 0.7 Hz, 1H), 7.83 (d, J=8.0 Hz, 1H), 7.77 (dd, J=8.8 and 1.9 Hz, 2H) 7.75 (t, J=7.8 Hz, 1H), 7.60 (s, 1H), 7.48 (t, J=7.8 Hz, 1H), 7.39 (s, 1H), 4.28 (septet, J=6.5 Hz, 1H), 1.52 (d, J=6.5 Hz, 6H);

$^{13}$C NMR ($CDCl_3$:$CD_3OD$=4:1): 166.30, 141.11, 138.27, 133.14, 132.67, 129.92, 128.78, 127.86, 127.67, 126.40, 124.37, 124.21, 67.66, 20.44.

EXAMPLE 2

Synthesis of 2-[3-(N-isopropyl)nitronyl]phenyl-1,2-benzisoselenazol-3(2H)-one (15)

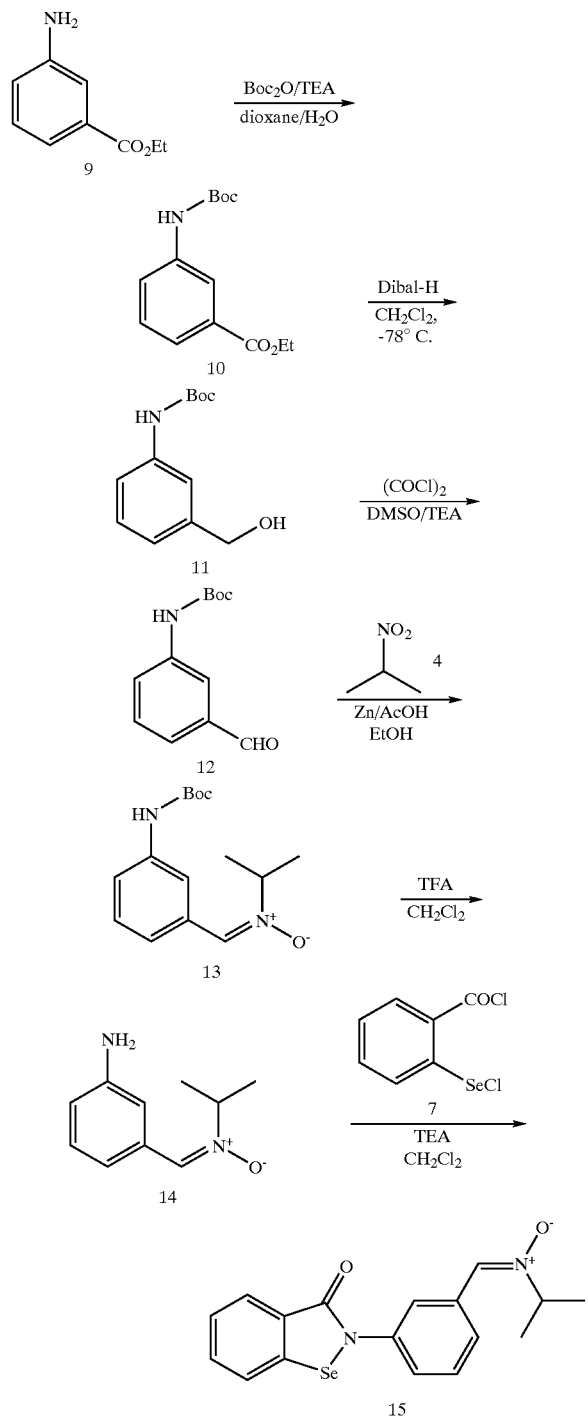

Step 1: Synthesis of ethyl 3-N-(1,1-dimethylethoxycarbonyl)aminobenzoate (10)

To a solution of 5.0 g (30.27 mmol) of ethyl 3-aminobenzoate (9) and 17 mL (0.12 mol) of triethylamine in 150 ml of 1,4-dioxane/H$_2$O (1:1 v/v) was added 16.52 g (75.67 mmol) of di-tert-butyl dicarbonate (Boc$_2$O). After stirring for 13 hours at room temperature, H$_2$O and diethyl ether were added. The organic layer was separated, washed with saturated NaCl solution, dried over anhydrous Na$_2$SO$_4$, filtered and concentrated under reduced pressure. The residue was purified by washing with n-hexanes to give 7.83 g (29.5 mmol) of compound 10 as a white solid in 98% yield.

$^1$H NMR (CDCl$_3$):7.90 (t, J=1.7 Hz, 1H), 7.71 (m, 2H), 7.36 (t, J=7.9 Hz, 1H), 6.63 (br s, 1H), 4.37 (m, 2H), 1.52 (s, 9H), 1.38 (t, J=7.1 Hz, 3H).

Step 2: Synthesis of 3-N-(1,1-dimethyl-ethoxycarbonyl)aminobenzyl alcohol (11)

To a solution of 9.64 g (36.34 mmol) of ethyl benzoate 10 in CH$_2$Cl$_2$ (200 mL) were added 109 mL of diisobutylaluminum hydride (DIBAL-H, 1.0 M soln in toluene) for 30 minutes at −78° C. After stirring for 3 hours at that temperature, 30 mL of MeOH was added slowly to the reaction mixture, and then the reaction mixture was warmed to room temperature. Diethyl ether and 0.5 N HCl solution were added and the organic layer was separated. The solution was re-extracted with diethyl ether. The combined organic layers were washed with saturated NaHCO$_3$ solution, dried over anhydrous Na$_2$SO$_4$, filtered, and concentrated under reduced pressure. The residue was purified by short flash column chromatography (silica, CH$_2$Cl$_2$:Hex:EtOAc=10:10:1 to 10:10:2) to give 7.2 g (32.3 mmol) of compound 11 in 89% yield.

$^1$H NMR (CDCl$_3$): 7.42 (s, 1H), 7.24 (m, 2H), 7.0 (t, J=6.9 Hz, 1H), 6.56 (s, 1H), 4.64 (s, 2H), 1.53 (s, 9H)

Step 3: Synthesis of 3-N-(1,1-dimethylethoxy-carbonyl)aminobenzaldehyde (12)

To a solution of 5.63 mL (64.50 mmol) of oxalyl chloride in CH$_2$Cl$_2$ (60 mL) was slowly added a solution of 6.92 mL (96.74 mmol) of DMSO in CH$_2$Cl$_2$ (60 mL) at −78° C. After 10 minutes, a solution of 7.2 g (32.3 mmol) of compound 11 in CH$_2$Cl$_2$ (60 mL) was added slowly and the reaction mixture was stirred for 30 minutes. 34 mL of TEA was added slowly. The reaction mixture was warmed to room temperature. CH$_2$Cl$_2$ and water were added and organic layer was separated. The organic layer was washed with saturated NaCl solution, dried over anhydrous Na$_2$SO$_4$, filtered and concentrated. The resulting solid was washed with n-hexane to give 6.55 g (29.60 mmol) of compound 12 as a white solid in 92% yield.

$^1$H NMR (CDCl$_3$):. 9.99 (t, J=3.4 Hz, 1H), 7.92 (t, 1H), 7.64 (d, 1H), 7.62 (d, 1H), 7.45 (t, 1H), 6.70 (s, 1H), 1.55 (s, 9H)

Step 4: Synthesis of N-isopropyl-α-[3-N-(1,1-dimethylethoxycarbonyl)amino ]phenyl nitrone(13)

6.55 g (29.6 mmol) of compound 12, 6.65 ml (74.03 mmol) of 2-nitropropane (4), and 6.78 g (103.65 mmol) of zinc were placed in a round-bottomed flask along with 95% ethanol (100 mL) and cooled to 0° C. 11.9 mL (207.9 mmol) of acetic acid was added slowly with stirring. The solution was allowed to come to room temperature, stirred for 12 hours. CH$_2$Cl$_2$ was added to the reaction mixture and it was filtered through a Celite pad and concentrated under reduced pressure. The residue was purified by short flash column chromatography (silica, CH$_2$Cl$_2$:EtOAc=1:2) to give 7.0 g (21.3 mmol) of compound 13 (mp: 189~191° C.) in 72% yield.

$^1$H NMR (CDCl$_3$): 8.37 (s, 1H), 7.8 (d, J=7.7 Hz, 1H), 7.5 (d, J=7.7 Hz, 1H), 7.42 (s, 1H), 7.33 (t, J=7.8 Hz, 1H), 6.60 (s, 1H), 4.19 (septet, J=6.5 Hz, 1H), 1.53 (s, 9H), 1.48 (d, J=6.5 Hz, 6H).

Step 5: Synthesis of N-isopropyl-α-3-aminophenyl nitrone (14)

To a solution of 5.0 g (17.96 mmol) of compound 13 in CH$_2$Cl$_2$ (200 mL) was added 20 mL of trifluoroacetic acid slowly at 0° C. The reaction mixture was warmed to room temperature and stirred for 16 hours. After concentration of the solution, the mixture was diluted with CH₂Cl₂ and saturated NaHCO₃ solution. The solution was saturated with NaCl and the organic layer was separated. The aqueous layer was extracted three times with CH₂Cl₂. The combined organic layers were dried over anhydrous Na₂SO₄ and concentrated under reduced pressure. The residue was purified by short flash column chromatography (silica, CH₂Cl₂:EtOAc:MeOH=5:5:1) to give 2.1 g (11.78 mmol) of compound 14 (mp: 103~106° C.) as a yellow solid in 66% yield.

$^1$H NMR (CDCl₃): 8.12 (t, 1H), 7.30 (s, 1H), 7.16 (d, 2H), 6.74 (m, 1H), 4.18 (septet, J=6.5 Hz, 1H), 3.74 (br s, 2H), 1.49 (d, J=6.5 Hz, 6H);

$^{13}$C NMR (CDCl₃): 147.11, 132.80, 131.88, 129.52, 119.87, 117.38, 114.77, 68.10, 21.24.

Step 6: Synthesis of 2-[3-(N-isopropyl)nitronyl]phenyl-1,2-benzisoselenazol-3(2H)-one (15)

To a solution of 50 mg (0.28 mmol) of compound 14 and 0.8 mL (5.62 mmol) of triethylamine in CH₂Cl₂ (3 mL) was slowly added 178 mg (0.70 mmol) of 2-chlorocarbonyl-benzeneselenenyl chloride (7) in CH₂Cl₂ (1.5 mL) at 0° C. After stirring for 4 hours at room temperature, the reaction mixture was concentrated under reduced pressure. The residue was purified by short flash column chromatography (silica, CH₂Cl₂:EtOAc =3:1 with 0 to 10% methanol) to give 60 mg (0.17 mmol) of compound 15 (mp: 94~980° C.) as a pale yellow solid in 60% yield.

$^1$H NMR (CDCl₃): 8.65 (m, 1H), 8.09 (m, 2H), 7.81 (m, 1H), 7.66 (m, 2H) 7.37 (m, 3H), 4.23 (septet, J=6.5 Hz, 1H), 1.52 (d, J=6.5 Hz, 6H);

$^{13}$C NMR (CDCl₃): 166.23, 139.77, 138.18, 133.00, 132.21, 131.79, 129.69, 127.95, 127.12, 126.96, 126.90, 125.17, 124.30, 68.53, 67.48, 21.33.

EXAMPLE 3

Synthesis of 5-chloro-2-[3-(N-isopropyl)-nitronyl]phenyl-1,2-benzisoselenazol-3(2H)-one (17)

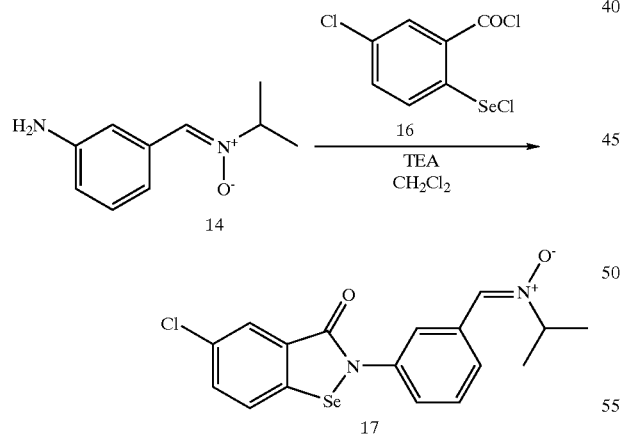

A similar procedure as that described for compound 8 in Example 1 provided 40 mg (0.10 mmol) of compound 17 as a yellow solid in 18% yield from 290 mg (1.01 mmol) of 4-chloro-2-chlorocarbonylbenzeneselenenyl chloride (16) and 100 mg (0.56 mmol) of N-isopropyl-α-3-aminophenylnitrone (14).

$^1$H NMR (CDCl₃:CD₃OD=4:1): 8.63 (t, J=1.7 Hz, 1H), 8.02 (d, J=2.2 Hz, 1H), 8.00 (d, J=7.9 Hz, 1H), 7.81 (dd, J=7.9 and 2.3 Hz, 1H), 7.81 (d, J=8.5 Hz, 1H), 7.61 (s, 1H), 7.61 (dd, J=8.5 and 2.3 Hz, 1H), 7.53 (t, J=7.9 Hz, 1H), 4.28 (septet, J=6.5 Hz, 1H), 1.50 (d, J=6.5 Hz, 6H);

$^{13}$C NMR (CDCl₃:CD₃OD=4:1): 166.30, 141.11, 138.27, 133.14, 132.67, 129.92, 128.77, 127.86, 127.67, 126.45, 124.37, 124.21, 67.66, 20.44.

EXAMPLE 4

Synthesis of 5-methyl-2-[3-(N-isopropyl)nitronyl]phenyl-1,2-benzisoselenazol-3(2H)-one (19)

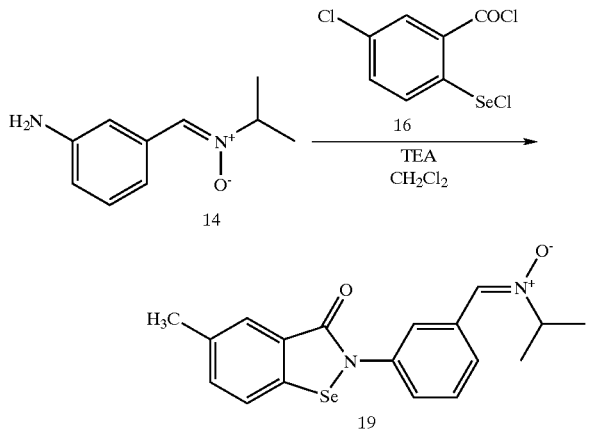

A similar procedure as that described for compound 8 in Example 1 provided 40 mg (0.20 mmol) of compound 19 (mp: 197~201° C.) as yellow solid in 30% yield from 380 mg (1.40 mmol) of 4-methyl-2-chlorocarbonylbenzeneselenenyl chloride (18) and 100 mg (0.56 mmol) of N-isopropyl-α-3-aminophenylnitrone (14).

$^1$H NMR (CDCl₃): 8.60 (s, 1H), 8.09 (d, J=7.7 Hz, 1H), 7.90 (s, 1H), 7.81 (d, J=8.0 Hz, 1H) 7.56 (d, J=8.0 Hz, 1H), 7.44 (m, 3H), 4.23 (septet, J=6.5 Hz, 1H), 2.47 (s, 3H), 1.51 (d, J=6.5 Hz, 6H);

$^{13}$C NMR (CDCl₃): 166.25,139.91, 137.07, 134.76, 134.39, 132.19, 131.78, 129.73, 129.71, 127.94, 127.09, 126.85, 125.14, 123.96, 68.51, 60.79, 21.41, 14.59.

EXAMPLE 5

Synthesis of 2-[4-(N-isopropyl)nitronyl]thiazol-2-yl-1,2-benzisoselenazol-3(2H)-one (26)

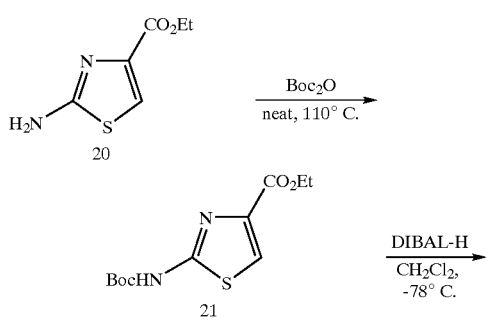

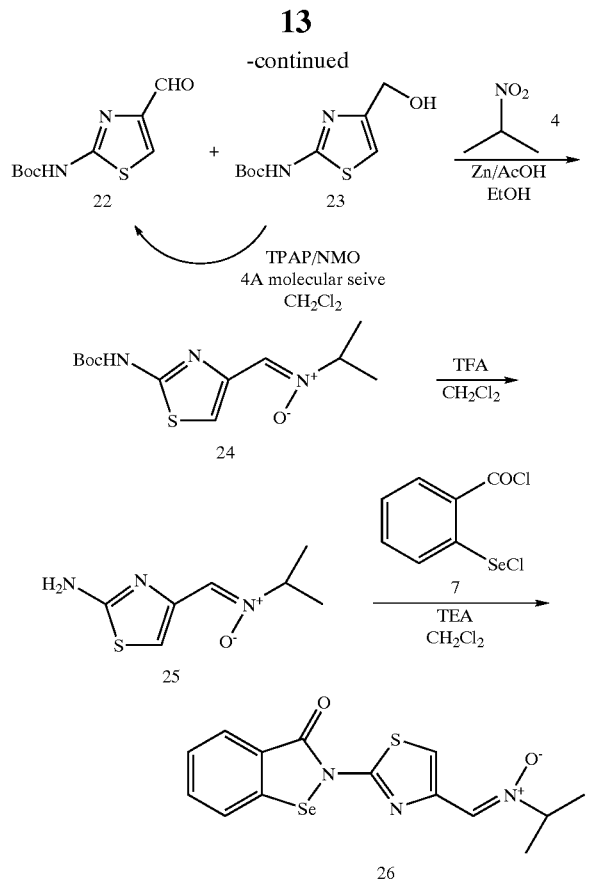

Step 1: Synthesis of ethyl 2-N-(1,1-dimethylethoxy-carbonyl)aminothiazole-4-carboxylate (21)

6.05 g (35.13 mmol) of aminothiazole 20 and 26.84 g (0.12 mmol) of di-tert-butyl dicarbonate (Boc$_2$O) were added into a flask and the mixture was heated for 24 hours at 110° C. The reaction mixture was cooled to room temperature and purified by short flash column chromatography (silica, CH$_2$Cl$_2$:Hex:EtOAc=10:6:3) to give 7.13g (26.18 mmol) of compound 21 as a white solid in 74.5% yield.

H NMR (CDCl$_3$): 8.21 (br s, 1H), 7.78 (s, 1H), 4.38 (q, J=7.1 Hz, 2H), 1.54 (s, J=7.1 Hz, 9H), 1.38 (t, 3H)

Step 2: Synthesis of 2-N-(1,1-dimethylethoxy-carbonyl) aminothiazole-4-carbaldehyde (22) (from ester 21)

To a solution of 7.0 g (25.71 mmol) of ethyl ester 21 in CH$_2$Cl$_2$ (75 mL) were added 77 mL of diisobutylaluminum hydride (DIBAL-H, 1.0 M soln in toluene) for 20 minutes at −78° C. After stirring for 3 hours at that temperature, 30 mL of MeOH was added slowly to the reaction mixture, and then the reaction mixture was warmed to room temperature. Diethyl ether and 0.5 N HCl solution were added and the organic layer was separated. The solution was re-extracted with diethyl ether. The combined organic layers were washed with saturated NaHCO$_3$ solution, dried over anhydrous Na$_2$SO$_4$, filtered, and concentrated under reduced pressure. The residue was purified by short flash column chromatography (silica, CH$_2$Cl$_2$:Hex:EtOAc=10:6:3 to CH$_2$Cl$_2$:EtOAc=1:1) to give 1.90 g (8.32 mmol) of solid aldehyde 22 in 32.4% yield and 3.5 g (15.20 mmol) of liquid alcohol 23 in 59.0% yield.

Aldehyde 22:
$^1$H NMR (CDCl$_3$): 9.88 (s, 1H), 8.83 (br s, 1H), 8.82 (s, 1H), 1.58 (s, 9H).

Alcohol 23:
$^1$H NMR (CDCl$_3$): 6.75 (s, 1H), 4.58 (s, 2H), 1.58 (s, 9H)

Step 2-1: Synthesis of 2-N-(1,1-dimethylethoxy-carbonyl) aminothiazole-4-carbaldehyde (22) (from alcohol 23)

To a solution of 2.04 g (8.597 mmol) of alcohol 23 in CH$_2$Cl$_2$ (50 mL) were added 302 mg (0.86 mmol) of TPAP (tetrapropylammonium perruthenate), 3.11 g (26.547 mmol) of NMO (N-methylmorpholine N-oxide) and 16 g (2 g/1 mmol of alcohol) of 4 molecular sieve. After stirring for 2 hours at room temperature, the reaction mixture was filtered through a Celite pad and concentrated under reduced pressure. The residue was purified by flash column chromatography (silica, CH$_2$Cl$_2$:Hex:EtOAc=10:6:3) to give 950 mg (4.0 mmol) of aldehyde 22in 46.5% yield.

Step 3: Synthesis of N-isopropyl-α-[2-N-(1,1-dimethylethoxycarbonyl)aminothiazol-4-yl]nitrone (24)

2.22 9 (9.72 mmol) of compound 22, 3.47g (33.65 mmol) of 2-nitropropane (4), and 2.54 g (38.84 mmol) of zinc were placed in a round-bottomed flask along with 95% ethanol (50 mL) and cooled to 0° C. 4.67 g (77.77 mmol) of acetic acid was added slowly with stirring. The solution was allowed to come to room temperature, stirred for 6 hours. CH$_2$Cl$_2$ was added to the reaction mixture and it was filtered through a Celite pad and concentrated under reduced pressure. The residue was purified by short flash column chromatography (silica, Hex:EtOAc=1:1) to give 2.51 g (8.80 mmol) of compound 24 in 90.5% yield.

$^1$H NMR (CDCl$_3$): 8.71 (s, 1H), 7.63 (S, 1H), 4.21 (septet, J=6.6 Hz, 1H), 1.55 (s, 9H), 1.49 (d, J=6.6 Hz, 6H)

Step 4: Synthesis of N-isopropyl-α-(2-aminothiazol-4-yl) nitrone (25)

To a solution of 2.44 g (8.55 mmol) of compound 24 in CH$_2$Cl$_2$ (30 mL) was added 3.3 mL of trifluoroacetic acid slowly at 0° C. The reaction mixture was warmed to room temperature and stirred for 16 hours. After concentration of the solution, the mixture was diluted with CH$_2$Cl$_2$ and saturated NaHCO$_3$ solution. The solution was saturated with NaCl and the organic layer was separated. The aqueous layer was extracted three times with CH$_2$Cl$_2$. The combined organic layers were dried over anhydrous Na$_2$SO$_4$ and concentrated under reduced pressure. The residue was purified by short flash column chromatography (silica, CH$_2$Cl$_2$:EtOAc:MeOH=5:5:1) to give 1.6 g (8.46 mmol) of compound 25 as a yellow solid in 99% yield.

$^1$H NMR (CDCl$_3$): 8.38 (s, 1H), 7.59 (s, 1H), 5.61 (b, 2H), 4.16 (septet, J=6.5 Hz, 1H), 1.46 (d, J=6.5 Hz, 6H).

Step 5: Synthesis of 2-[4-(N-isopropyl)nitronyl]thiazol-2-yl-1,2-benzisoselenazol-3(2H)-one (26)

To a solution of 100 mg (0.53 mmol) of compound 25 and 0.74 mL (5.29 mmol) of triethylamine in CH$_2$Cl$_2$ (15 mL) was slowly added 220 mg (0.866 mmol) of 2-chlorocarbonyl-benzeneselenenyl chloride (7) in CH$_2$Cl$_2$ (5 mL) at 0° C. After stirring for 1 hour at room temperature, the reaction mixture was concentrated under reduced pressure. The residue was purified by recrystallization (MeOH/CH$_2$Cl$_2$) to give 70 mg (0.19 mmol) of compound 26 as a pale yellow solid in 37% yield.

$^1$H NMR (CD$_3$OD): 8.82 (s, 1H), 8.15 (s, 1H), 8.05 (d, J=7.8 Hz, 1H), 8.03 (d, J=8.0 Hz, 1H), 7.75 (t, J=7.3 Hz, 1H), 7.53 (t, J=7.4 Hz, 1H), 4.43 (septet, J=6.8 Hz, 1H), 1.50 (d, J=6.8 Hz, 6H).

EXAMPLE 6

Synthesis of 2-[4-(N-t-butyl)nitronyl]thiazol-2-yl-1,2-benzisoselenazol-3(2H)-one

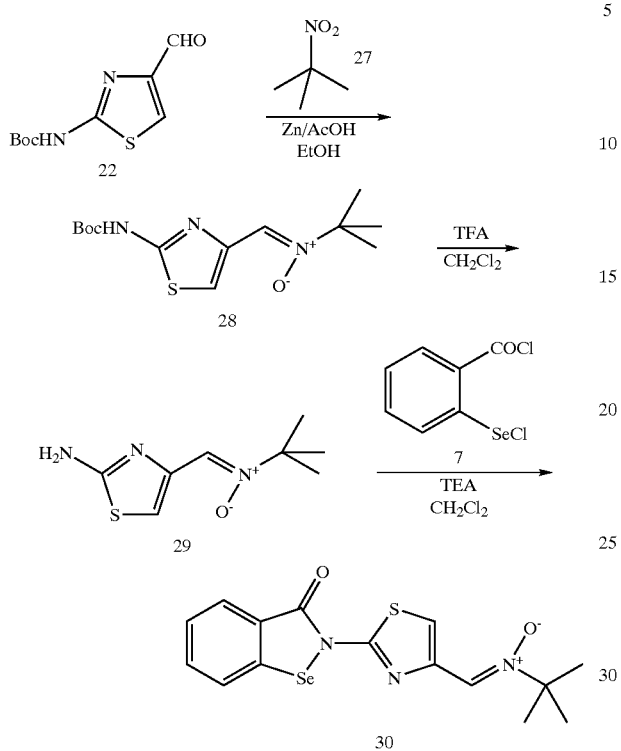

Step 1: Synthesis of N-tert-butyl-α-[2-N-(1,1-dimethylethoxycarbonyl)aminothiazol-4-yl]nitrone (28)

2.0 g (8.76 mmol) of compound 22, 5.42g (52.57 mmol) of 2-methyl-2-nitropropane (27), and 2.86 g (43.81 mmol) of zinc were placed in a round-bottomed flask along with 95% ethanol (50 mL) and cooled to 0° C. 4.21 g (70.11 mmol) of acetic acid was added slowly with stirring. The solution was allowed to come to room temperature, stirred for 6 hours. $CH_2Cl_2$ was added to the reaction mixture and it was filtered through a Celite pad and concentrated under reduced pressure. The residue was purified by short flash column chromatography (silica, Hex:EtOAc=1:1) to give 1.28 g (4.28 mmol) of compound 28 as a yellow solid in 49% yield.

$^1$H NMR ($CDCl_3$): 9.9 (br s, 1H), 8.82 (s, 1H), 7.87 (s, 1H), 1.60 (s, 9H), 1.54 (s, 6H);
$^{13}$C NMR ($CDCl_3$): 159.54, 152.35, 141.53, 125.78, 117.31, 82.83, 70.33, 28.27, 28.21.

Step 2: Synthesis of N-tert-butyl-α-(2-aminothiazol-4-yl)nitrone (29)

To a solution of 200 mg (0.668 mmol) of compound 28 in $CH_2Cl_2$ (10 mL) was added 381 mg of trifluoroacetic acid slowly at 0° C. The reaction mixture was warmed to room temperature and stirred for 14 hours. After concentration of the solution, the mixture was diluted with $CH_2Cl_2$ and saturated $NaHCO_3$ solution. The solution was saturated with NaCl and the organic layer was separated. The aqueous layer was extracted three times with $CH_2Cl_2$. The combined organic layers were dried over anhydrous $Na_2SO_4$ and concentrated under reduced pressure. The residue was purified by short flash column chromatography (silica, EtOAc) to give 111 mg (0.56 mmol) of compound 29 as a yellow solid in 83% yield.

$^1$H NMR (MeOD): 8.29 (s, 1H), 7.82 (s, 1H), 4.91 (s, 2H), 1.54 (s, 9H)

$^{13}$C NMR (MeOD): 168.76, 141.94, 127.57, 114.24, 70.23, 27.20.

Step 3: Synthesis of 2-[4-(N-t-butyl)nitronyl]thiazol-2-yl-1,2-benzisoselenazol-3(2H)-one (30)

To a solution of 100 mg (0.50 mmol) of compound 29 and 0.70 mL (5.02 mmol) of triethylamine in $CH_2Cl_2$ (15 mL) was slowly added 180 mg (0.703 mmol) of 2-chlorocarbonyl-benzeneselenenyl chloride (7) in $CH_2Cl_2$ (5 mL) at 0° C. After stirring for 1 hour at room temperature, the reaction mixture was concentrated under reduced pressure. The residue was purified by short flash column chromatography (silica, EtOAc:Hex=1:1) to give 67 mg (0.176 mmol) of compound 30 as a pale yellow solid in 35% yield.

$^1$H NMR ($CDCl_3$:$CD_3OD$=10:1): 8.80 (s, 1H), 8.04 (d, J=7.6 Hz, 1H), 7.91 (s, 1H), 7.60 (d, J=7.86 Hz, 1H), 7.61 (t, J=7.2 Hz, 1H), 7.40 (t, J=7.41 Hz, 1H), 1.56 (s, 9H)

$^{13}$C NMR ($CDCl_3$:$CD_3OD$=10:1): 165.38, 157.10, 140.74, 139.19, 133.71, 128.76, 127.05, 126.78, 124.72, 119.43, 70.54, 28.05.

EXAMPLE 7

Synthesis of 2-[4-(N-isopropyl)nitronyl]benzyl-1,2-benzisoselenazol-3(2H)-one (37)

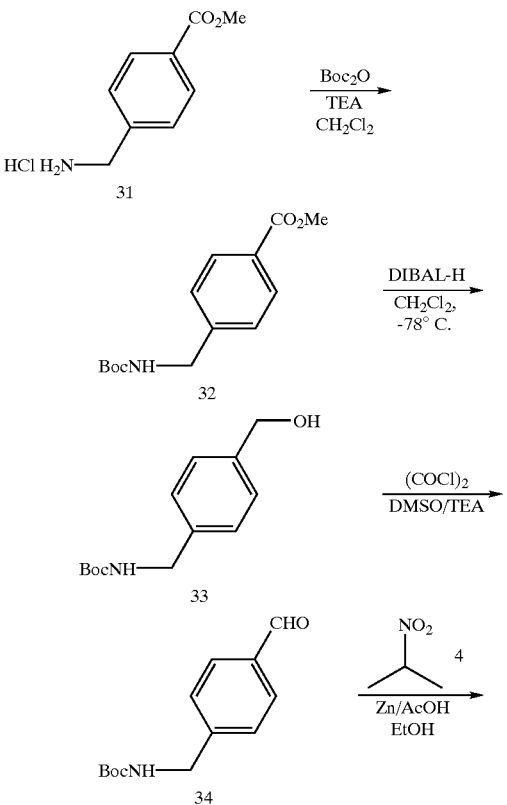

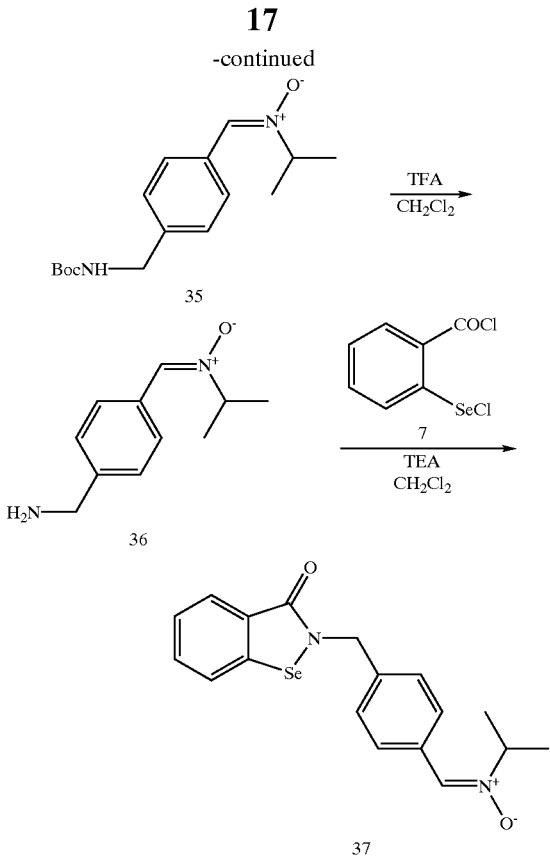

Step 1: Synthesis of methyl 4-N-(1,1-dimethylethoxycarbonyl)aminomethylbenzoate (32)

To a solution of 500 mg (2.48 mmol) of methyl 4-aminomethylbenzoate HCl salt (31) in $CH_2Cl_2$ (10 mL) were added 753 mg (7.45 mmol) of TEA and 568 mg (2.60 mmol) of $Boc_2O$ in $CH_2Cl_2$ (1 mL) at 0° C. After 30 minutes, the reaction mixture was warmed to room temperature. After additional stirring for 4 hours, $CH_2Cl_2$ was added to the reaction solution. The organic layer was washed with 0.1 N HCl solution, dried over $MgSO_4$, filtered, and concentrated under reduced pressure. The residue was purified by flash column chromatography (silica, Hex:EtOAc=1:1) to give 620 mg of compound 32 in 94% yield.

$^1$H NMR ($CDCl_3$): 7.58 (d, J8.2 Hz, 2H), 7.34 (d, J=8.2 Hz, 2H), 4.90 (br s, 1H), 4.37 (d, 2H), 3.91 (s, 3 H), 1.46 (s, 9H);
$^{13}$C NMR ($CDCl_3$): 167.02, 156015, 144042, 130.03, 129.23, 127.27, 79.91, 52.23, 44.43, 28.49

Step 2: Synthesis of 4-N-(1,1-dimethylethoxy-carbonyl)aminomethylbenzyl alcohol (33)

To a solution of 620 mg (2.34 mmol) of ethyl benzoate 32 in $CH_2Cl_2$ (15 mL) was added 7.01 mL of diisobutylaluminum hydride (DIBAL-H, 1.0 M soln in toluene) for 30 minutes at −78° C. After stirring for 3 hours at that temperature, 3 mL of MeOH was added slowly to the reaction mixture, and then the reaction mixture was warmed to room temperature. Diethyl ether and 0.5 N HCl solution were added and the organic layer was separated. The solution was re-extracted with diethyl ether. The combined organic layers were washed with saturated $NaHCO_3$ solution, dried over anhydrous $Na_2SO_4$, filtered, and concentrated under reduced pressure. The residue was purified by short flash column chromatography (silica, Hex:EtOAc=2:1) to give 520 mg (2.19 mmol) of compound 33 in 94% yield.

$^1$H NMR ($CDCl_3$): 7.32 (m, 4H), 4.80 (br s, 1H), 4.68 (s, 2H), 4.31 (m, 2H), 1.46 (s, 9H);
$^{13}$C NMR ($CDCl_3$): 156.6, 140.19, 138.30, 127.69, 127.33, 79.67, 64.95, 44.44, 28.49

Step 3: Synthesis of 4-N-(1,1-dimethylethoxy-carbonyl)aminomethylbenzaldehyde (34)

To a solution of 0.48 mL (5.48 mmol) of oxalyl chloride in $CH_2Cl_2$ (2 mL) was slowly added a solution of 0.63 mL (8.76 mmol) of DMSO in $CH_2Cl_2$ (2 mL) at −78° C. After 15 minutes, a solution of 520 mg (2.19 mmol) of compound 33 in $CH_2Cl_2$ (3 mL) was added slowly and the reaction mixture was stirred for 30 minutes. 2.5 mL of TEA was added slowly. The reaction mixture was warmed to room temperature. $CH_2Cl_2$ and $H_2O$ were added and organic layer was separated. The organic layer was washed with saturated NaCl solution, dried over anhydrous $Na_2SO_4$, filtered, and concentrated under reduced pressure. The residue was purified by short flash column chromatography (silica, Hex:EtOAc=2:1) to give 510 mg (2.17 mmol) of compound 34 in 99% yield.

$^1$H NMR ($CDCl_3$): 9.99 (s, 1H), 7.85 (d, J=7.9 Hz, 2H), 7.44 (d, J=7.9 Hz, 2H), 4.95 (br s, 1H), 4.40 (d, 2H), 1.47 (s, 9H);
$^{13}$C NMR ($CDCl_3$): 191.95, 156.01, 146.37, 135.24, 129.93, 127.53, 79.57, 44.13, 28.28

Step 4: Synthesis of N-isopropyl-α-[4-N-(1,1-dimethylethoxycarbonylamino)methylphenyl]nitrone (35)

500 mg (2.13 mmol) of compound 34, 0.44 mL (4.84 mmol) of 2-nitropropane (4), and 565 mg (8.64 mmol) of zinc were placed in a round-bottomed flask along with 95% ethanol (10 mL) and cooled to 0° C. 0.83 mL of acetic acid was added slowly with stirring. The solution was allowed to come to room temperature, stirred for 6 hours. $CH_2Cl_2$ was added to the reaction mixture and it was filtered through a Celite pad and concentrated under reduced pressure. The residue was purified by short flash column chromatography (silica, Hex:EtOAc=1:1) to give 540 mg (1.85 mmol) of compound 35 in 87% yield.

$^1$H NMR ($CDCl_3$): 8.21 (d, J=8.2 Hz, 2H), 7.42 (s, 1H), 7.32 (d, J=8.2 Hz, 2H), 4.86 (br s, 1H), 4.33 (m, 2H), 4.23 (septet, J=6.5 Hz, 1H), 1.50 (d, J=6.5 Hz, 6H), 1.45 (s, 9H);
$^{13}$C NMR ($CDCl_3$): 156.00, 141.33, 131.80, 129.62, 128.78, 127.28, 79.42, 67.64, 44.36, 28.37, 20.83

Step 5: Synthesis of N-isopropyl-α-(4-aminomethyl-phenyl) nitrone (36)

To a solution of 200 mg (0.68 mmol) of compound 35 in $CH_2Cl_2$ (3 mL) was added 0.34 mL of trifluoroacetic acid slowly at 0° C. The reaction mixture was warmed to room temperature and stirred for 6 hours. After concentration of the solution, the mixture was diluted with $CH_2Cl_2$ and saturated $NaHCO_3$ solution. The solution was saturated with NaCl and the organic layer was separated. The aqueous layer was extracted three times with $CH_2Cl_2$. The combined organic layers were dried over anhydrous $Na_2SO_4$ and concentrated under reduced pressure. The residue was purified by short flash column chromatography (silica, EtOAc:MeOH=9:1 to 4:1) to give 130 mg (0.68 mmol) of compound 36 as a yellow solid in 99% yield.

$^1$H NMR ($CDCl_3$): 8.10 (d, J=8.4 Hz, 2H), 7.45 (s, 1H), 7.34 (d, J=8.4 Hz, 2H), 4.13 (septet, J=6.54 Hz, 1H), 3.88 (s, 2H), 1.41 (d, J6.54 Hz, 6H);
$^{13}$C NMR ($CDCl_3$): 137.05, 135.89, 132.38, 130.98, 130.05, 68.80, 43.92, 20.90

Step 6: Synthesis of 2-[4-(N-isopropyl)-nitronyl]benzyl-1,2-benzisoselenazol-3(2H)-one (37)

To a solution of 80 mg (0.42 mmol) of compound 36 and 0.29 mL (2.08 mmol) of triethylamine in $CH_3CN$ (15 mL)

and EtOH (1 mL) was slowly added 138 mg (0.54 mmol) of 2-chlorocarbonylbenzeneselenenyl chloride (7) in CH$_3$CN (4 mL) at 0° C. After stirring for 4 hours at room temperature, the reaction mixture was concentrated under reduced pressure. The residue was purified by short flash column chromatography (silica, EtOAc) to give 70 mg (0.19 mmol) of compound 37 as a pale yellow solid in 45% yield.

$^1$H NMR (CDCl$_3$): 8.24 (d, J=8.1 Hz, 2H), 8.04 (d, J=7.9 Hz, 1H), 7.91 (s, 1H), 7.87 (d, J=6.4 Hz, 1H), 7.63 (d, J=6.8 Hz, 1H), 7.45 (t, J=6.9 Hz, 1H), 7.37 (d, J=8.1 Hz, 2H), 4.95 (s, 2H), 4.34 (septet, J=63 Hz, 1H), 1.36 (d, J=6.3 Hz, 6H);

$^{13}$C NMR (CDCl$_3$): 140.12, 139.24, 131.99, 130.73, 129.20, 128.66, 128.06, 126.29, 125.79, 68.09, 48.21, 21.021

EXAMPLE 8

Synthesis of 7-Nitro-2-[4-(N-isopropyl)nitronyl]phenyl-1,2-benzisoselenazol-3(2H)-one (40)

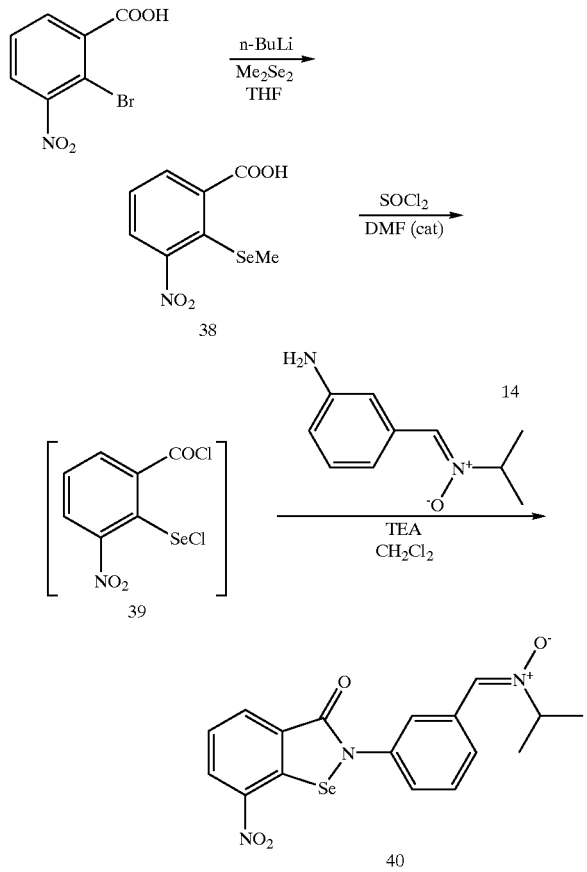

Step 1: Synthesis of 2-Methylseleno-3-nitrobenzoic acid (38)

To a solution of 500 mg (2.0 mmol) of 2-bromo-3-nitrobenzoic acid in anhydrous THF (15 mL) was added 2.80 mL (4.47 mmol) of n-BuLi (1.6 M soln. in Hex.) slowly at −78° C. After 10 minutes, a solution of 383 mg (2.03 mmol) of dimethyl diselenide in THF (5 mL) was added. After 30 minutes, the reaction mixture was warmed to room temperature. After additional stirring for 2 hours, ethyl acetate was added. The organic layer was washed with 1 N HCl solution, dried over MgSO$_4$, and concentrated under reduced pressure. 470 mg of crude product was obtained and used for the next reaction without further purification.

$^1$H NMR (CD$_3$OD): 7.91 (d, J=7.85 Hz, 1H), 7.88 (d, J=7.86 Hz, 1H), 7.56 (t, J=7.85 Hz, 1H), 2.31 (s, 3H).

Step 2: Synthesis of 7-Nitro-2-[4-(N-isopropyl)-nitronyl]phenyl-1,2-benzisoselenazol-3(2H)-one (40)

470 mg of crude product 38 was refluxed with 4 mL of SOCl$_2$ for 4 hours. After removal of excess thionyl chloride, the crude product 39 was dissolved in CH$_2$Cl$_2$ (10 mL). To a solution of 100 mg (0.56 mmol) of compound 14 and 0.568 mg (5.61 mmol) of triethylamine in CH$_2$Cl$_2$ (15 mL) was slowly added 3 mL of compound 39 solution obtained in the above at 0° C. After stirring for 2 hours at room temperature, the reaction mixture was concentrated under reduced pressure. The residue was purified by short flash column chromatography (silica, EtOAc) to give 121 mg (0.30 mmol) of compound 40 in 53% yield.

$^1$H NMR (CDCl$_3$): 8.79 (s, 1H), 8.61 (d, J=8.07 Hz, 1H), 8.49 (d, J=7.56 Hz, 1H), 8.03 (d, J=7.76 Hz, 1H), 7.87 (d, J=8.10 Hz, 1H), 7.76 (t, J=7.71 Hz, 1H), 7.55 (s, 2H), 4.28 (septet, J=6.63 Hz, 1H), 1.56 (d, J=6.51 Hz, 6H);

$^{13}$C NMR (CDCl$_3$): 164.03, 142.11, 138.78, 136.52, 135.27, 132.16, 131.42, 131.25, 129.66, 127.95, 127.77, 127.08, 126.41, 124.16, 68.33, 21.05.

Using the procedures described in Examples 1–8 above and the appropriate starting materials and reagents, the following seleno compounds containing nitrone moiety could be prepared:

2-[2-(N-isopropyl)nitronyl]-phenyl-1,2-benzisoselenazol-3(2H)-one;

2-[2-(N-tert-butyl)nitronyl]-phenyl-1,2-benzisoselenazol-3(2H)-one;

5-fluoro-2-[2-(N-isopropyl)nitronyl]-phenyl-1,2-benzisoselenazol-3(2H)-one;

5-chloro-2-[2-(N-isopropyl)nitronyl]-phenyl-1,2-benzisoselenazol-3(2H)-one;

5-bromo-2-[2-(N-isopropyl)nitronyl]-phenyl-1,2-benzisoselenazol-3(2H)-one;

5-methyl-2-[2-(N-isopropyl)nitronyl]-phenyl-1,2-benzisoselenazol-3(2H)-one;

5-methoxy-2-[2-(N-isopropyl)nitronyl]-phenyl-1,2-benzisoselenazol-3(2H)-one;

6-chloro-2-[2-(N-isopropyl)nitronyl]-phenyl-1,2-benzisoselenazol-3(2H)-one;

6-methyl-2-[2-(N-isopropyl)nitronyl]-phenyl-1,2-benzisoselenazol-3(2H)-one;

5-nitro-2-[2-(N-isopropyl)nitronyl]-phenyl-1,2-benzisoselenazol-3(2H)-one ;

7-nitro-2-[2-(N-isopropyl)nitronyl]-phenyl-1,2-benzisoselenazol-3(2H)-one;

6,7-methylenedioxy-2-[2-(N-isopropyl)nitronyl]-phenyl-1,2-benzisoselenazol-3(2H)-one;

2-[3-(N-isopropyl)nitronyl]-phenyl-1,2-benzisoselenazol-3(2H)-one;

2-[4-(N-isopropyl)nitronyl]-phenyl-1,2-benzisoselenazol-3(2H)-one;

2-[4-(N-isopropyl)nitronyl]-benzyl-1,2-benzisoselenazol-3(2H)-one;

2-[4-(N-isopropyl)nitronyl]-phenylethyl-1,2-benzisoselenazol-3(2H)-one;

2-[4-(N-isopropyl)nitronyl]-pyridin-2-yl-1,2-benzisoselenazol-3(2H)-one;

2-[5-(N-isopropyl)nitronyl]-pyridin-2-yl-1,2-benzisoselenazol-3(2H)-one;

2-[4-(N-isopropyl)nitronyl]-pyrimidin-2-yl-1,2-benzisoselenazol-3(2H)-one;

2-[5-(N-isopropyl)nitronyl]-pyrimidin-2-yl-1,2-benzisoselenazol-3(2H)-one;

2-[5-(N-isopropyl)nitronyl]-furan-2-yl-1,2-benzisoselenazol-3(2H)-one;

2-[5-(N-isopropyl)nitronyl]-thiophen-2-yl-1,2-benzisoselenazol-3(2H)-one;

2-[4-(N-isopropyl)nitronyl]-thiazol-2-yl-1,2-benzisoselenazol-3(2H)-one;

2-[4-(N-isopropyl)nitronyl]-oxazol-2-yl-1,2-benzisoselenazol-3(2H)-one;

2-[2-(N-isopropyl)nitronyl]-1H-imidazol-4-yl-1,2-benzisoselenazol-3(2H)-one;

2-[2-(N-isopropyl)nitronyl]-1-methyl-1H-imidazol-4-yl-1,2-benzisoselenazol-3(2H)-one;

2-[5-(N-isopropyl)nitronyl]-1H-pyrrol-3-yl-1,2-benzisoselenazol-3(2H)-one;

2-[5-(N-isopropyl)nitronyl]-1-methyl-1H-pyrrol-3-yl-1,2-benzisoselenazol-3(2H)-one;

2-[6-(N-isopropyl)nitronyl]-benzothiazol-2-yl-1,2-benzisoselenazol-3(2H)-one;

2-[5-(N-isopropyl)nitronyl]-2H-[1,2,4]-triazol-3-yl-1,2-benzisoselenazol-3(2H)-one;

2-[5-(N-isopropyl)nitronyl]-2-methyl-2H-[1,2,4]-triazol-3-yl-1,2-benzisoselenazol-3(2H)-one.

EXAMPLE 9

Determination of Water Solubility

A standard solution was prepared by dissolving a precisely weighed amount (generally 1 mg) of the test compounds in 1 mL of methanol. With a Beckman DUI® 7500 Spectrophotometer, the UV absorption maximum of each compound was determined by eventually diluting the solution with MeOH as necessary.

A saturated solution of each compound was then prepared by stirring magnetically a small volume of 10 mM phosphate buffer (pH 7.4) in the presence of an excess test compound for 3 hours. The obtained saturated solution was filtered in order to remove solid compound through a Gelman 0.45 m filter and scanned by UV at the wavelength of the absorption maximum previously determined.

Total solubility was determined by the following equation: C'=A'(C/A), where C=concentration of standard solution (mg/mL); A=absorbance of standard solution; A'=absorbance of the saturated solution; C'=concentration of the saturated solution (mg/mL) (see: Protein Sci., 7: 556–563, (1998)). The results are summarized in Table 1.

It can be clearly seen from the table 1 that the compounds of the present invention have much better water solubility than Ebselen has.

EXAMPLE 10

Inhibition of Lipid Peroxidation

The compounds of the present invention were tested for antioxidant effect in terms of the repression of the radical chain reaction of a multilayer liposome.

The liposome was prepared as followings: 30 mg of commercially available soybean phosphatidylcholine (PC, Sigma Chemical Co., U.S.A.) was dissolved in 1 mL of ethanol, and 200 of the ethanol/PC solution was added to 10 mL of 10 mM Tris buffer including 50 mM NaCl (pH 7.0) with stirring.

The ability of a compound to inhibit oxidation of the liposome was evaluated as followings: To 400 of the liposomes were added the test compound (in buffer or ethanol) and histidine-$FeCl_3$ (167:33 $\mu$M final). Oxidation was initiated by the addition of $FeCl_2$ (33 $\mu$M final prepared in nitrogen purged water). The mixtures were shaken at 37° C. for 15 minutes. Thereafter, tubes were treated with 1 mL of 0.67% thiobarbituric acid (TBA): 10% trichloroacetic acid (2:1, v/v) in 0.25 N HCl solution, containing 1.5% (v/v) t-butylhydroxytoluene (BHT) to terminate oxidation. The aliquots were heated to 100° C. for 20 minutes. After ice cooling, 1 mL of chloroform was added to 1 mL of supernatant from tubes and tubes were centrifuged. The absorbances of the resulting supernatant were measured at 532 nm (see: Table 2).

TABLE 2

| | Inhibitor Concentration ($IC_{50}$) |
|---|---|
| Example 1 | 81.1 $\mu$M |
| Example 2 | 111.0 $\mu$M |
| Example 5 | 1.2 $\mu$M |
| Example 7 | 246.5 $\mu$M |
| S-PBN | 25.0 mM |
| Ebselen | 148.3 $\mu$M |

It can be seen from the Table 2 that the compounds of the invention, especially the compound obtained in example 5 have better LPO inhibition activity than the reference compounds S-PBN and Ebselen (the most promising antioxidant currently and is in clinical phase III).

TABLE 1

| Compounds | Ebselen | Example 1 | Example 2 | Example 5 | Example 7 |
|---|---|---|---|---|---|
| Amount added (mg) | 5.71 | 5.14 | 5.55 | 5.74 | 5.02 |
| Wavelength (determined) | 330 nm | 314 | 294 | 302 | 300 |
| Measured Abs. | 0.0284 | 0.6096 | 0.3584 | 0.1827 | 1.2276 |
| Dilution factor | 1 | 1 | 10 | 10 | 1 |
| A' | 0.0284 | 0.6096 | 3.584 | 1.827 | 1.2276 |
| A | 0.6154 | 1.6807 | 1.2729 | 0.8082 | 0.8871 |
| C ($\mu$M) | 100 | 50 | 50 | 50 | 50 |
| C' ($\mu$M) = A' (C/A) | 4.615 | 18.135 | 140.781 | 113.029 | 69.192 |
| C' (g/L = mg/mL) | 0.001265 | 0.006516 | 0.050580 | 0.041403 | 0.025830 |

EXAMPLE 11

Measurement of Glutathione Peroxidase Activity

Glutathione peroxidase like activity was determined by the reduction of GSSG formed via the NADPH-glutathione reductase system as an indicator system.

To 350 of 50 mM Tris-HCl(pH 7.6) containing 5 mM of EDTA (assay buffer) are added in the following order:

1) 350 of assay buffer containing 6.4 mM of reduced glutathione (GSH), 640 $\mu$M of nicotinamide adenine dinucleotide (NADPH), and 1.6 unit/mL of glutathione disulfide reductase (GR)
2) 70 of 800 $\mu$M of the test compound which was dissolved in DMSO (i.e., each compound was tested at a final concentration of 50 $\mu$M)
3) 350 of 0.007% tert-butyl hydroperoxide which was made by 1/10,000 dilution of tert-butyl hydroperoxide with DDW.

The final reaction volume is 1120.

The reaction was carried out at 25° C. The glutathione peroxidase activity is assayed by measuring the decrease of absorbance at 340 nm for 3 minutes. The said activity or initial enzymatic rate is proportional to the slope of the variation of absorbance with time.

The catalytic activity for oxygen reduction of the compounds tested corresponds to the rate of consumption of NADPH.

The results of the glutathione peroxidase activity measurements are shown in Table 3 below. They are expressed in n-moles of NADPH consumed per minute.

TABLE 3

| Compound | Rate $A_{340/min(30-300\ sec)}$ | Rate/0.00622 (nmol NADPH/ min/mL) | % Ebselen |
|---|---|---|---|
| Ebselen | −0.118 | 18.97 | 100 |
| Example 1 | −0.141 | 22.67 | 119.50 |
| Example 2 | −0.125 | 20.10 | 105.96 |
| Example 5 | −0.125 | 20.13 | 106.11 |
| Example 7 | −0.084 | 13.50 | 71.17 |

As shown in Table 3 above, the compounds of general formula (I) described in the invention catalyze the reduction of an organic hydroperoxide, in the presence of glutathione and glutathione disulfide reductase. Thus, it is noted that the compounds of the invention possess a significant and specific glutathione peroxidase activity.

EXAMPLE 12

Protection of Neuron Cells

EXAMPLE 12-1

The Culture of Neuron Cells of Cerebral Cortex

Mixed cortical cell cultures, containing both neuronal and glial elements, were prepared from fetal ICR (Institute Cancer Research) mice at 14–15 days of gestation. Briefly, dissociated cortical cells were plated onto previously established glial monolayer culture at 2.5 hemispheres per 24-multiwell plate (Nunc, U.S.A.). The plating medium consisted of Eagle's minimal essential medium (Earle's salts, supplied glutamine-free) supplemented with glucose (final concentration, 20 mM), 2 mM glutamine, 5% fetal bovine serum, and 5% horse serum. Ten mM cytosine arabinoside was added to the medium 5–6 days after the plating to halt the growth of non-neuronal cells. Cultures were maintained at 37° C. in a humidified $CO_2$ incubator (5%) and used for experiments after between 10–14 days in vitro (DIV).

The glial feeder cultures were prepared from neocortices of postnatal (1–3 day-old) mice. Dissociated cortical cells were plated at 0.25 hemispheres per 24-multiwell plate, in plating medium supplemented with 5% fetal bovine serum, and 10% horse serum. With this method, most neurons do not survive, but astrocytes do, resulting in astrocyte-rich cultures. Glial cultures were grown to confluency for 10–30 days, when they were used to generate mixed cortical cultures.

EXAMPLE 12-2

Protection of Cortical Neuronal Cell Death Induced by $Fe^{2+}$ ion

When ferrous iron is placed in normoxic solution, it autooxidizes to produce ROS in the form of hydroxyl radicals, superoxide anion free radicals, and hydrogen peroxide.

Cortical cell cultures prepared in Example 12-1 were exposed for 24 hours to 30 mM $FeCl_2$ (Fe), to induce neuronal cell death. 24 hours exposure to toxin with or without test compounds was done in serum free Eagle's minimal essential medium (MEM) supplemented with 20 mM glucose and 38 mM sodium bicarbonate in 5% $CO_2$ incubator at 37° C. All of compounds were dissolved in DMSO at high concentrations, and then diluted to final concentrations in the exposure medium at the time of addition.

Methods of measuring cell death were as follows:

Overall cell injury was first estimated in all experiments by examination of cultures under phase-contrast microscope. The morphological assessments were usually performed one day after exposure to toxins, at which point the process of cell death was largely completed.

In addition, overall neuronal cell injury was quantitatively estimated by measuring the activity of lactate dehydrogenase (LDH), released by damaged or destroyed cells, into the extracellular fluid. A small amount of LDH was always present in the media of cultures that underwent the same exposure procedures but without the addition of toxins (sham wash controls). This background amount, determined on sister sham wash controls within each experiment, was subtracted from values obtained in toxin-treated cultures. The absolute value of the LDH efflux produced by toxin exposure was quite consistent within sister cultures of single plating, but varied somewhat in cultures of different platings. This variability is largely a function of resultant neuronal density (which varied despite constant original plating densities, presumably reflecting small variations in cell preparation or serum characteristics). Therefore, each LDH value was scaled to the maximal neuronal LDH release (=100) after 24 hours exposure to 30 $\mu$M $FeCl_2$ (Fe), in sister cultures, where near complete neuronal death with no glial damage occurs. Numbers greater than 100 usually indicate additional astroglial cell injury.

FIG. 1 is a graph showing the results of combined treatment of Ebselen and $Fe^{2+}$ toxin.

Figure 2:
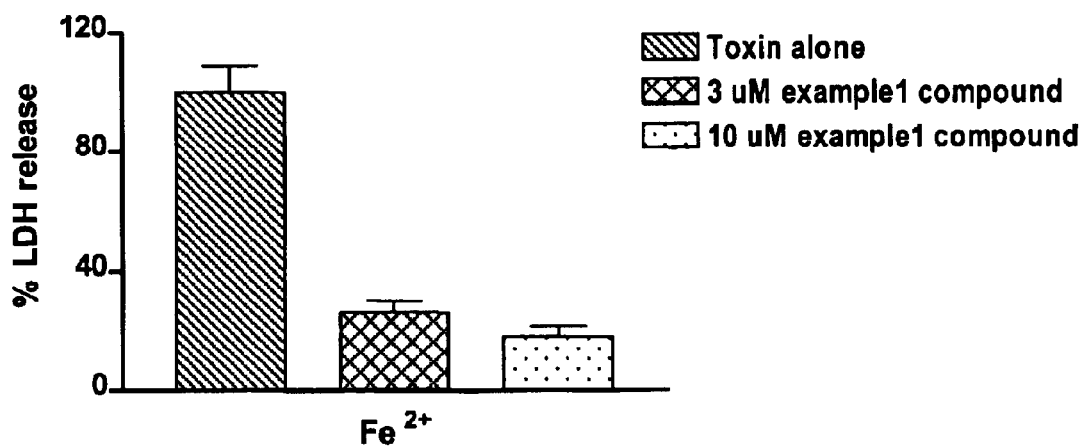
FIG. 2 is a graph showing the results of combined treatment of compound obtained in Example 1 and $Fe^{2+}$ toxin.

FIG. 2 is a graph showing the results of combined treatment of compound obtained in Example 1 and $Fe^{2+}$ toxin.

Figure 3:
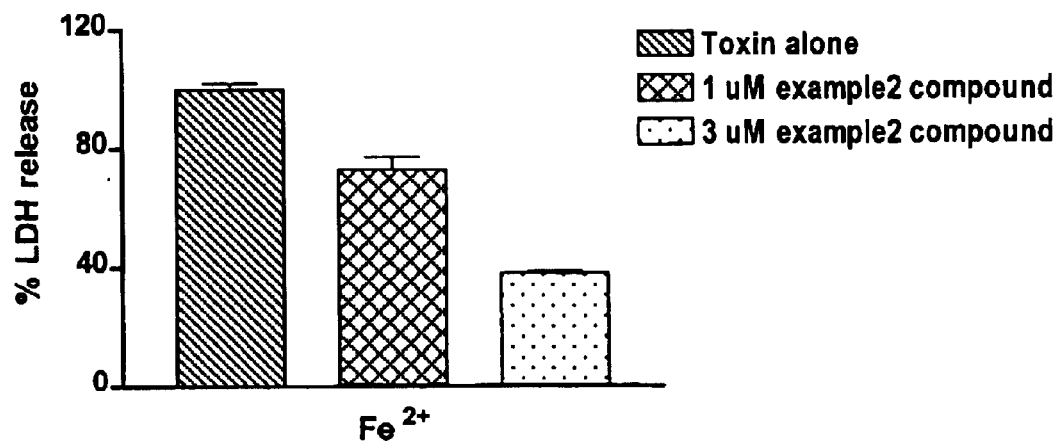
FIG. 3 is a graph showing the results of combined treatment of compound obtained in Example 2 and $Fe^{2+}$ toxin.

FIG. 3 is a graph showing the results of combined treatment of compound obtained in Example 2 and $Fe^{2+}$ toxin.

Figure 4:
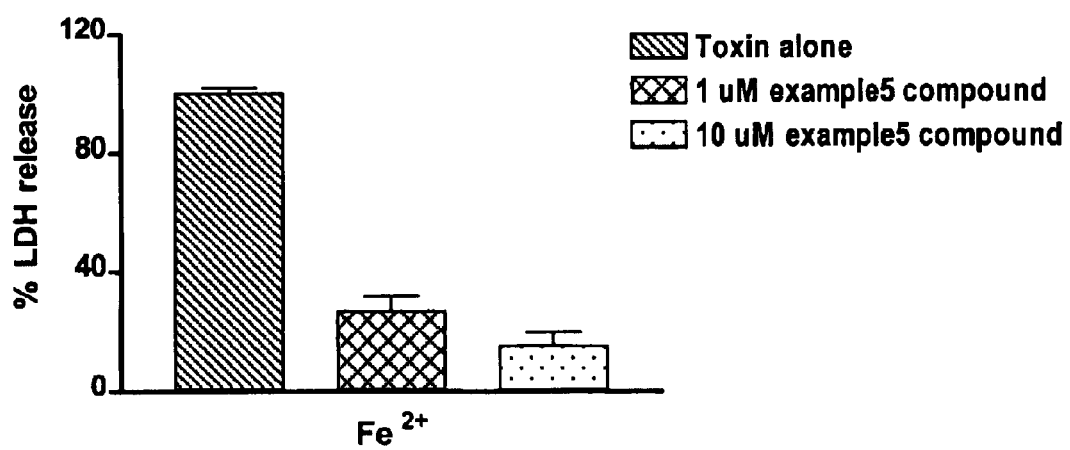
FIG. 4 is a graph showing the results of combined treatment of compound obtained in Example 5 and $Fe^{2+}$ toxin.

FIG. 4 is a graph showing the results of combined treatment of compound obtained in Example 5 and $Fe^{2+}$ toxin.

Figure 5:
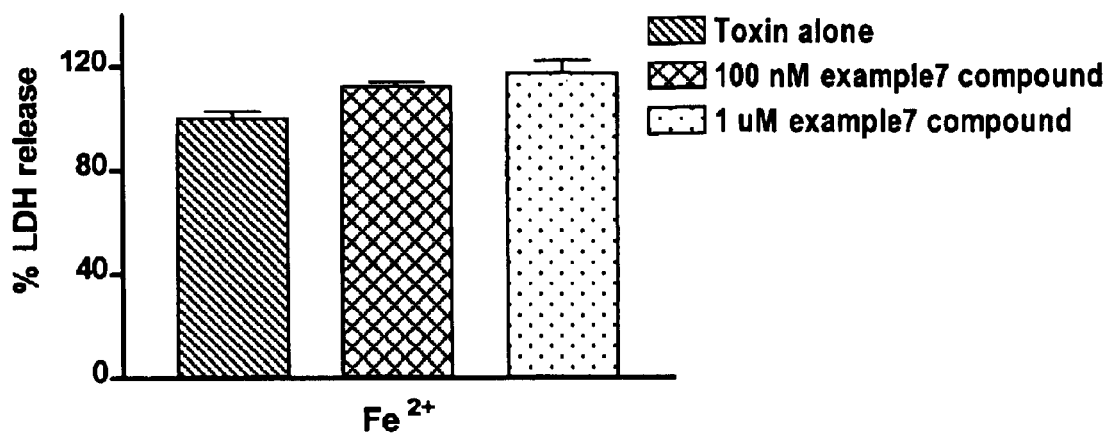
FIG. 5 is a graph showing the results of combined treatment of compound obtained in Example 7 and $Fe^{2+}$ toxin.

FIG. 5 is a graph showing the results of combined treatment of compound obtained in Example 7 and $Fe^{2+}$ toxin.

As can be seen in FIGS. 1 to 5, it was clearly demonstrated that the compounds of the invention effectively protected the neuronal cell death by $Fe^{2+}$ toxin

EXAMPLE 13

Toxicity of the Compounds on the Neuron Cells

The viability of cortical cell prepared in Example 12-1 was quantified by lactate dehydrogenase (LDH) assay after exposure for 24 hours to the different concentrations of the test compound. Twenty four hours exposure to the compound was done in serum free Eagle's minimal essential medium (MEM) supplemented with 20 mM glucose and 38 mM sodium bicarbonate in 5% $CO_2$ incubator at 37° C. All of compounds were dissolved in DMSO at high concentrations, and then diluted to final concentrations in the exposure medium at the time of addition.

Measurement of cell death was the same as the method in the Example 12-2.

Figure 6:
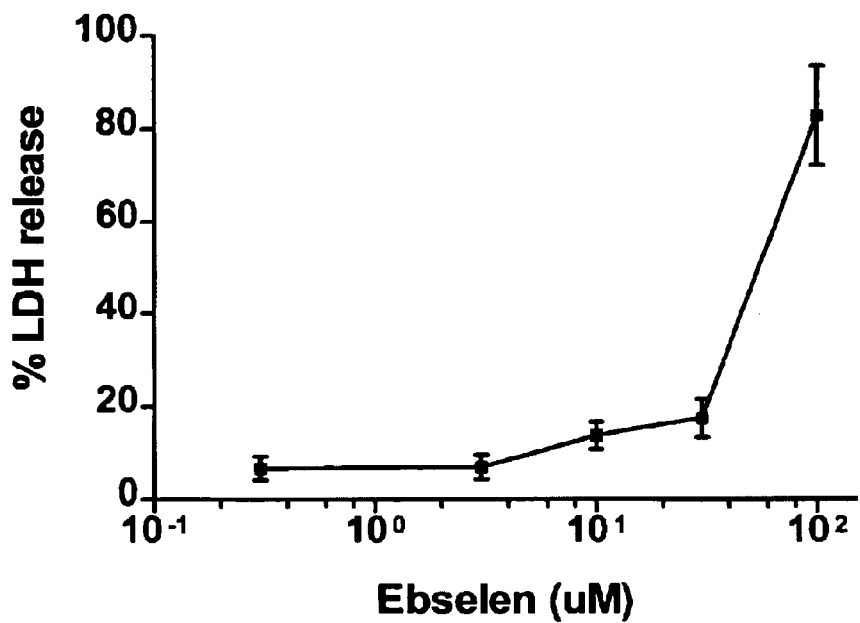
FIG. 6 is a graph showing the level of cell damage as the treatment concentration of Ebselen increases.

FIG. 6 is a graph showing the level of cell damage as the treatment concentration of Ebselen increases.

Figure 7:
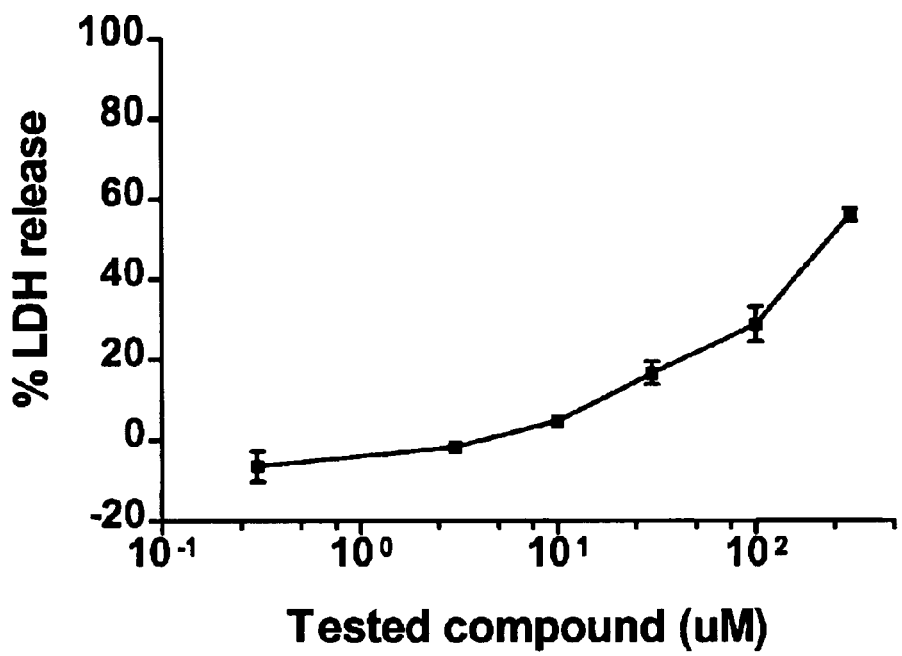
FIG. 7 is a graph showing the level of cell damage as the treatment concentration of compound obtained in Example 1 increases.

FIG. 7 is a graph showing the level of cell damage as the treatment concentration of compound obtained in Example 1 increases.

Figure 8:
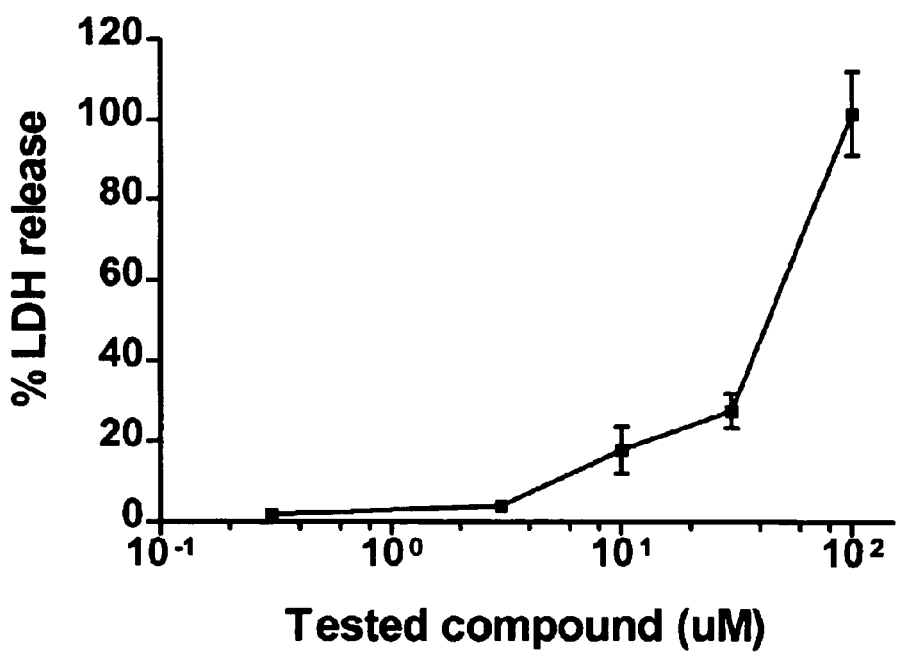
FIG. 8 is a graph showing the level of cell damage as the treatment concentration of compound obtained in Example 2 increases.

FIG. 8 is a graph showing the level of cell damage as the treatment concentration of compound obtained in Example 2 increases.

Figure 9:
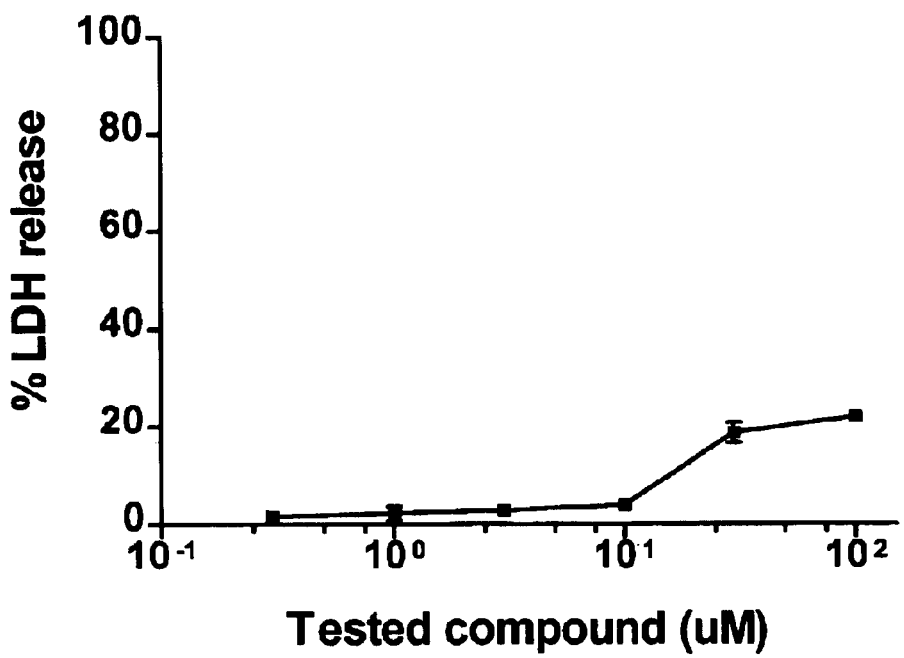
FIG. 9 is a graph showing the level of cell damage as the treatment concentration of compound obtained in Example 5 increases.

FIG. 9 is a graph showing the level of cell damage as the treatment concentration of compound obtained in Example 5 increases.

Figure 10:
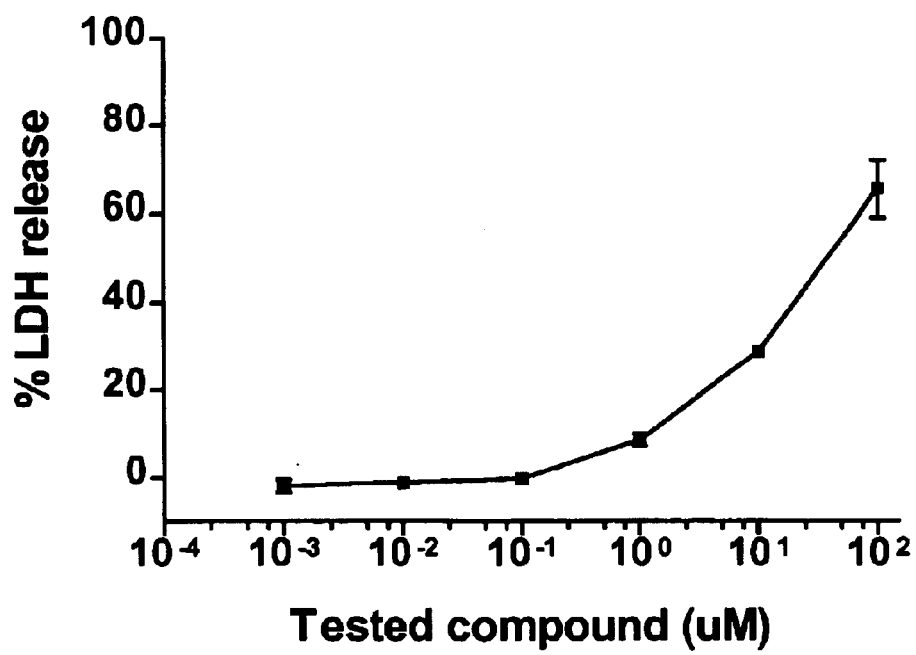
FIG. 10 is a graph showing the level of cell damage as the treatment concentration of compound obtained in Example 7 increases.

FIG. 10 is a graph showing the level of cell damage as the treatment concentration of compound obtained in Example 7 increases.

As can be seen in FIGS. 6 to 10, it was clearly determined that the compounds of the invention exhibit lower cytotoxicity than Ebselen, assuring that they can be administered at large doses in a safe manner.

EXAMPLE 14

Protection of Cell Damage by Ischemia (in vivo)

Male Mongolian gerbils (Meriones unguiculatus) weighing 80–88 g were used in the present study. Each animal was medicated P.O. with vehicle, Ebselen or various test compounds (60 mg/kg in 10% DMSO), after 30 minutes ischemic injury, respectively. 20 animals were allotted into every group. The animals were placed under general anesthesia with a mixture of 2.5% isoflurane in 33% oxygen and 67% nitrous oxide. A midline ventral incision was made in the neck. Both common carotid arteries were isolated, freed of nerve fibers, and occluded using nontraumatic aneurysm clips. Complete interruption of blood flow was confirmed by observing the central artery in eyeballs using ophthalmoscope. After five minutes of occlusion, the aneurysm clips were removed from both common carotid arteries. Restoration of blood flow (reperfusion) was observed directly under the microscope. Sham-operated controls were subjected to the same surgical procedures except that common carotid arteries were not occluded. Body temperature was monitored and maintained at 37° C.±0.5° C. during surgery and during the immediate postoperative period until the animals recovered fully from anesthesia. At the designated reperfusion time (4 days), operated animals and sham animals were killed.

Animals were perfused transcardially with phosphate-buffered saline (PBS, pH 7.4) followed by 4% paraformaldehyde in 0.1 M phosphate buffer (pH 7.4) at 4 days (n=7) after surgery. The brains were removed, and postfixed in the same fixative for 4 hours. The brain tissues were cryoprotected by infiltration with 30% sucrose overnight. Cornoy fixed specimens were cut into 30 sections on a cryostat, were sequentially stained by Cresyl violet dye.

Images of staining in the hippocampus of each animal were captured with an Applescanner. The brightness and contrast of each image file were uniformly enhanced by Adobe Photoshop version 2.4.1, followed by analysis using NIH Image 1.59 software. All data obtained from the quantitative data were analyzed using one-way ANOVA to determine statistical significance. Bonferroni's test was used for post-hoc comparisons. P values below 0.05 or 0.01 were considered statistically significant.

Figure 11A:
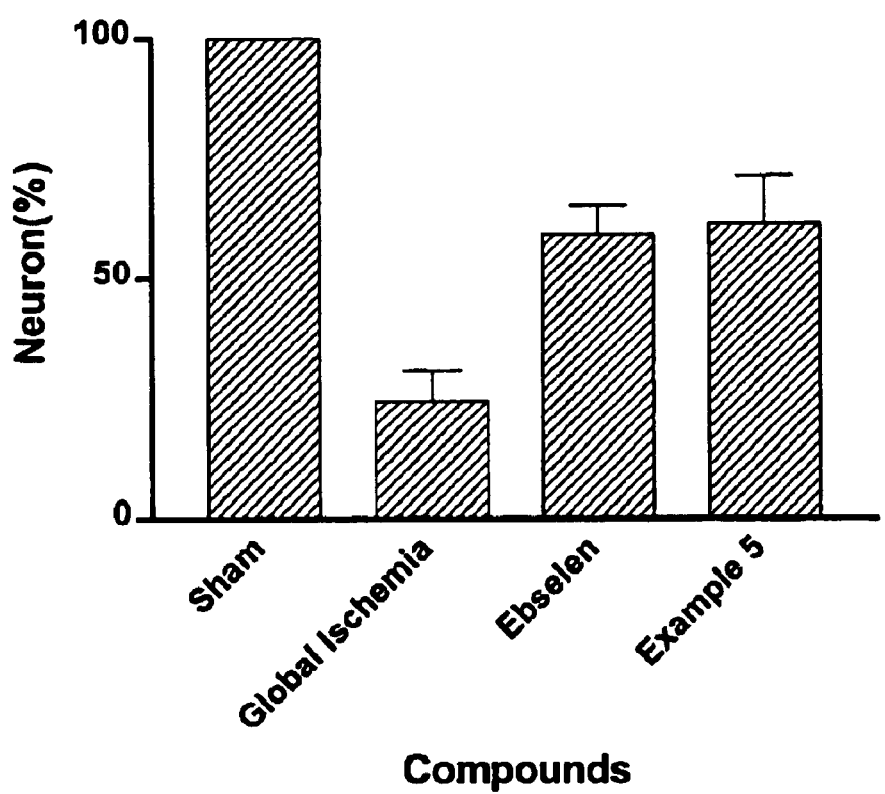
FIG. 11-a is a graph showing the protection level of cell damage in case of the treatment of the compound of the invention after ischemia.
Figure 11B:
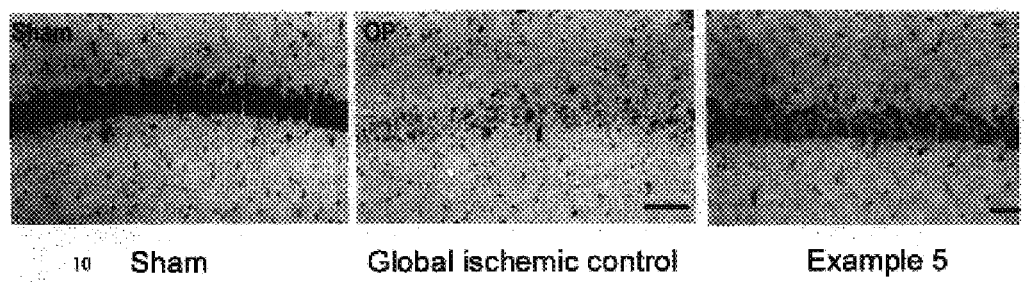

FIG. 11-$a$ is a graph showing the protection level of cell damage in case of the treatment of the compound of the invention after ischemia.

FIG. 11-$b$ is a photomicrograph showing the protection level of cell damage in case of the treatment of the compound of the invention after ischemia.

As the results, the test compound prepared in Example 5 has more neuroprotective effects against ischemic neuronal degeneration than Ebselen. The compound synthesized in Example 5 showed that the protective effects was 61% in post-treated groups. In the Ebselen—treated groups, the effect was 59%.

In conclusion, we suggest that the compound prepared in Example 5 may be a promising candidate as a potential drug for the treatment of ischemia associated diseases.

As clearly described and illustrated above, the present invention provides novel seleno compounds containing nitrone moiety, a process for preparing the same, the use of the novel compounds as therapeutics for treating and/or preventing various medical diseases arising from ROS. The compounds of the invention possess similar or superior lipid peroxidation (LPO) inhibition activity to the reference compounds of S-PBN and Ebselen. While showing lower toxicity and better water solubility, they also effectively inhibit the cerebral neuronal cell death caused by ROS and show neuroprotective effects against ischemic neuronal degeneration.

From the foregoing description, various modifications and changes in the compositions and methods of this invention will occur to those skilled in the art. All such modifications coming within the scope of the appended claims are intended to be included therein.

What is claimed is:

1. Seleno compounds containing nitrone moiety with the following formula (I), and pharmaceutically acceptable salts thereof:

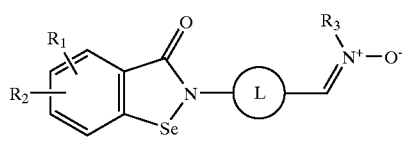

wherein, $R_1$ and $R_2$ which may be the same or different from each other, represent hydrogen, halogen, $C_{1-4}$-alkyl, $C_{1-4}$-alkoxy, hydroxy, trifluoromethyl, nitro, or $R_1$ and $R_2$ together denote methylenedioxy;

L denotes phenyl, $C_{1-4}$-alkylphenyl, heterocyclic unsaturated or saturated radical having 1 to 4 heteroatoms of elements nitrogen, oxygen, and/or sulfur from the group comprising furanyl, oxazolyl, isooxazolyl, thiophenyl, thiazolyl, isothiazolyl, pyrrolyl, imidazolyl, pyrazolyl, thiadiazolyl, pyridyl, pyrimidinyl, pyrazinyl, pyridazinyl, benzothiazolyl, benzoimidazolyl, benzotriazolyl, triazinyl, triazolyl, it being possible for the heterocyclic radical to be substituted once or twice, identically or differently, by halogen, $C_{1-2}$-alkyl, $C_{1-4}$-alkoxy, $C_{1-4}$-alkylthio, hydroxy, mercapto, trifluoromethyl, nitro, phenyl, nitrile, carboxy or $C_{1-4}$-alkoxycarbonyl; and, $R_3$ represents alkyl, substituted alkyl, alkenyl, alkynyl, aralkyl, aryl, cycloalkyl or cycloalkenyl.

2. The compounds according to claim 1, wherein $R_1$ and $R_2$ are selected from the group consisting of hydrogen, fluorine, chlorine, bromine, methyl, ethyl, propyl, butyl, hydroxy, methoxy, trifluoromethyl and nitro, or $R_1$ and $R_2$ together denote methylenedioxy;

L is selected from the group consisting of phenyl, benzyl, ethylphenyl, and heterocyclic unsaturated or saturated radical having 1 to 4 heteroatoms of elements mtrogen, oxygen, and/or sulfur from the group comprising furanyl, oxazolyl, thiophenyl, thiazolyl, pyrrolyl, imidazolyl, pyridyl, pyrimidinyl, benzothiazolyl, benzotriazolyl, triazolyl, it being possible for the heterocyclic radical to be substituted once or twice, identically or differently, by fluorine, chlorine, bromine, methyl, ethyl, hydroxy, methoxy, ethoxy, methylsulfanyl, phenylsulfanyl, trifluoromethyl, nitro, phenyl, nitrile, carboxy, methoxycarbonyl, or ethoxycarbonyl; and, $R_3$ is selected from the group consisting of alkyl, substituted alkyl, aralkyl, aryl and cycloalkyl.

3. The compounds according to claim 2, wherein $R_1$ and $R_2$ are selected from the group consisting hydrogen, chlorine, bromine, methyl, ethyl, hydroxy, methoxy, trifluoromethyl, and nitro, or $R_1$ and $R_2$ together denote methylenedioxy;

L is selected from the group consisting of phenyl, benzyl, ethylphenyl, and heterocyclic unsaturated or saturated radical having 1 to 4 heteroatoms of elements nitrogen, oxygen, and/or sulfur from the group comprising furanyl, oxazolyl, thiophenyl, thiazolyl, pyrrolyl, imidazolyl, pyridyl, pyrimidinyl, it being possible for the heterocyclic radical to be substituted once or twice, identically or differently, by chlorine, methyl, methoxy, methylsulfanyl, phenylsulfanyl, trifluoromethyl, nitro, nitrile, carboxy, methoxycarbonyl, or ethoxycarbonyl; and, $R_3$ is selected from the group consisting of alkyl, substituted alkyl and cycloalkyl.

4. A process for preparing the compound of formula (I) defined in claim 1, which comprises the following steps of:

(i) reacting an N-protected aminealdehydes having a proper linkers (L) (1) with an alkylhydroxylamines ($R_3$NHOH) to give a nitrones (2);

(ii) deprotecting the nitrone compounds (2) obtained in step (i) to produce a free amine nitrones (3); and, (iii) reacting the free amines of the compounds (3) obtained in step (ii) with o-chloroselenobenzoyl chloride (4) in the presence of an excessive amount of a base to generate the compound of the formula (I) defined in claim 1, wherein the above steps are illustrated in the following reaction formulas,

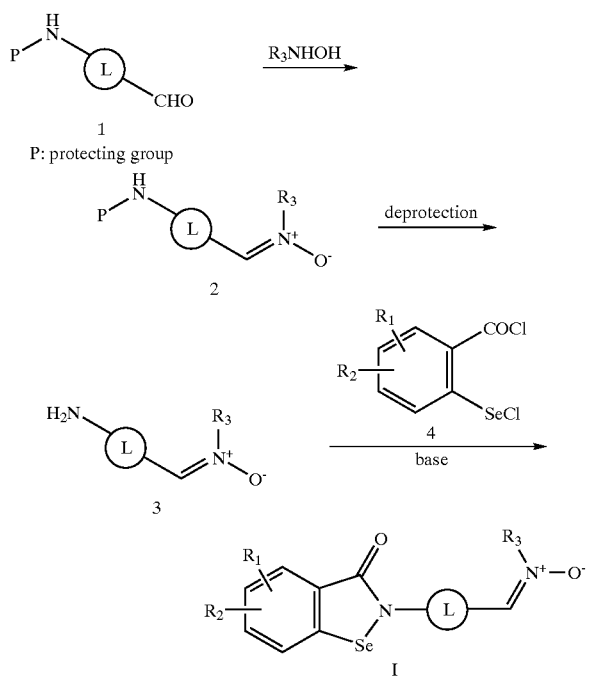

5. The processes according to claim 4, wherein alkylhydroxylamines of the step (i) are generated in situ from nitroalkanes, zinc, and acetic acid.

6. The process according to claim 4, wherein the step (ii) is carried out by removing the protecting group with trifluoroacetic acid in case the protecting group is tert-butoxycarbonyl, or alkali base such as LiOH in case the protecting group is acetyl.

7. The process according to claim 4, wherein the base of the step (iii) is an organic base.

8. The process according to claim 7, wherein the organic base is triethylamine.

9. A pharmaceutical composition which comprises as an active ingredient an effective amount of the compound of formula (I) defined in claim 1, in combination with one or more pharmaceutically acceptable carriers or excipients.

10. The pharmaceutical composition according to claim 9, wherein the carrier is an oral carrier.

11. The pharmaceutical composition according to claim 9, wherein the carrier is an injectable carrier.

12. A method for treating a living body afflicted with a condition requiring an antioxidant agent, which comprises a step of administering to the living body an amount of the compound of formula (I) defined in claim 1 which is effective for alleviation of one or more symptoms of said condition.

13. A method for treating a living body with an acute or progressive neurodegenerative disorders, which comprises a step of administering to the living body an amount of the compound of formula (I) defined in claim 1 which is effective for alleviation of one or more symptoms of said disorders.

14. The method according to claim 13, wherein the acute or progressive neurodegenerative disorder is selected from the group consisting of stroke, Parkinson's disease and Alzheimer's disease.

15. The method according to claim 13, wherein the living body exhibits symptoms of stroke.

* * * * *